(12) United States Patent
Jacobs et al.

(10) Patent No.: US 11,400,454 B2
(45) Date of Patent: Aug. 2, 2022

(54) MODULAR MOBILE FIELD-DEPLOYABLE LABORATORY FOR RAPID, ON-SITE DETECTION AND ANALYSIS OF BIOLOGICAL TARGETS

(71) Applicant: MRIGlobal, Kansas City, MO (US)

(72) Inventors: Jonathan L. Jacobs, Rockville, MD (US); Joseph A. Russell, Arlington, VA (US); Jacob R. Aspinwall, Palm Bay, FL (US)

(73) Assignee: MRIGlobal, Kansas City, MO (US)

( * ) Notice: Subject to any disclaimer, the term of this patent is extended or adjusted under 35 U.S.C. 154(b) by 661 days.

(21) Appl. No.: 16/185,178

(22) Filed: Nov. 9, 2018

(65) Prior Publication Data

US 2019/0076844 A1    Mar. 14, 2019

Related U.S. Application Data

(63) Continuation-in-part of application No. 15/866,073, filed on Jan. 9, 2018, now abandoned.

(Continued)

(51) Int. Cl.
*B01L 9/02* (2006.01)
*A45F 4/02* (2006.01)
(Continued)

(52) U.S. Cl.
CPC .............. *B01L 9/02* (2013.01); *A45C 5/04* (2013.01); *A45C 5/14* (2013.01); *A45C 7/005* (2013.01);

(Continued)

(58) Field of Classification Search
CPC ............... B01L 9/02; B01L 2200/028; B01L 2200/087; B01L 2200/04; B01L 2300/0618; B01L 2200/10
(Continued)

(56) References Cited

U.S. PATENT DOCUMENTS 5,429,432 A    7/1995  Johnson
6,241,688 B1   6/2001  Bouda et al.
(Continued)

FOREIGN PATENT DOCUMENTS

CN    205433910 U  *  8/2016
RU      2056944 C1     3/1996

OTHER PUBLICATIONS

Zhang Yunqi, "English Machine Translation of CN-205433910-U". Translated on Aug. 22, 2021.*

(Continued)

*Primary Examiner* — Liban M Hassan
(74) *Attorney, Agent, or Firm* — Husch Blackwell LLP

(57) ABSTRACT

A mobile field-deployable laboratory to more conveniently enable the detecting, sequencing and analyzing of biological agents at the point-of-need. This device enables field operators to go from sample to actionable information in the field without the need for an internet connection or grid-based power. The present mobile laboratory is configured in a footlocker configuration including a plurality of different compartments specifically configured for holding all of the necessary equipment for use in a wide variety of different applications including successfully extracting, amplifying, (Continued)

sequencing and characterizing specific viruses, pathogens and other bacteria directly in the field including an integrated power supply for providing power to the relevant components for up to 72 hours of continuous use without the need for any external power source. The present mobile laboratory includes a deployable workbench area which provides a stable workstation when the footlocker configuration is deployed.

35 Claims, 19 Drawing Sheets

Related U.S. Application Data

(60) Provisional application No. 62/444,569, filed on Jan. 10, 2017.

(51) Int. Cl.
| | | |
|---|---|---|
| *C12Q 1/686* | (2018.01) | |
| *A45F 3/04* | (2006.01) | |
| *A45C 5/04* | (2006.01) | |
| *B01L 1/00* | (2006.01) | |
| *A45C 5/14* | (2006.01) | |
| *A45C 7/00* | (2006.01) | |
| *A45F 3/00* | (2006.01) | |
| *A45C 9/00* | (2006.01) | |

(52) U.S. Cl.
CPC .............. *A45F 3/04* (2013.01); *A45F 4/02* (2013.01); *B01L 1/52* (2019.08); *C12Q 1/686* (2013.01); *A45C 2009/002* (2013.01); *A45F 2003/003* (2013.01); *B01L 2200/028* (2013.01); *B01L 2200/04* (2013.01); *B01L 2200/087* (2013.01); *B01L 2200/10* (2013.01); *B01L 2200/18* (2013.01); *B01L 2300/027* (2013.01); *B01L 2300/0618* (2013.01)

(58) Field of Classification Search
USPC ........................................... 435/287.2
See application file for complete search history.

(56) References Cited

U.S. PATENT DOCUMENTS

| | | | |
|---|---|---|---|
| 6,305,185 B1* | 10/2001 | Sloan .................... | A45C 5/14 |
| | | | 62/235.1 |
| 7,857,957 B2 | 12/2010 | Cheng et al. | |
| 7,870,937 B1 | 1/2011 | Arnao | |
| 9,623,782 B1 | 4/2017 | Coons | |
| 9,678,088 B2 | 6/2017 | Whitesides et al. | |
| 2006/0281101 A1 | 12/2006 | Dzenitis et al. | |
| 2007/0159781 A1 | 7/2007 | Zbikowski | |
| 2007/0255595 A1 | 11/2007 | Nickell | |
| 2008/0240837 A1 | 10/2008 | Green | |
| 2009/0117608 A1 | 5/2009 | Quessy et al. | |
| 2011/0070578 A1* | 3/2011 | Bell .................. | B01L 3/502753 |
| | | | 435/6.19 |
| 2014/0265760 A1 | 9/2014 | Layne et al. | |
| 2015/0204598 A1 | 7/2015 | Affleck et al. | |
| 2016/0367017 A1 | 12/2016 | Adams et al. | |
| 2017/0206329 A1 | 7/2017 | Capocasale et al. | |
| 2017/0223947 A1 | 8/2017 | Gall et al. | |

OTHER PUBLICATIONS

International Search Report and Written Opinion dated Jan. 16, 2020.
Miller, Portable Laboratory For Detection And Monitoring of Hazardous Chemicals, U.S. Statutory Invention Registration No. H431, Feb. 2, 1988.
http://www.forestry-suppliers.com/product_pages/products.php?mi=75151, Dec. 21, 2017.
https://hannainst.com/hi3817bp-backpack-lab-water-quality-educational-test-kit.html, Dec. 21, 2017.

* cited by examiner

PACKED 1

PACKED 2

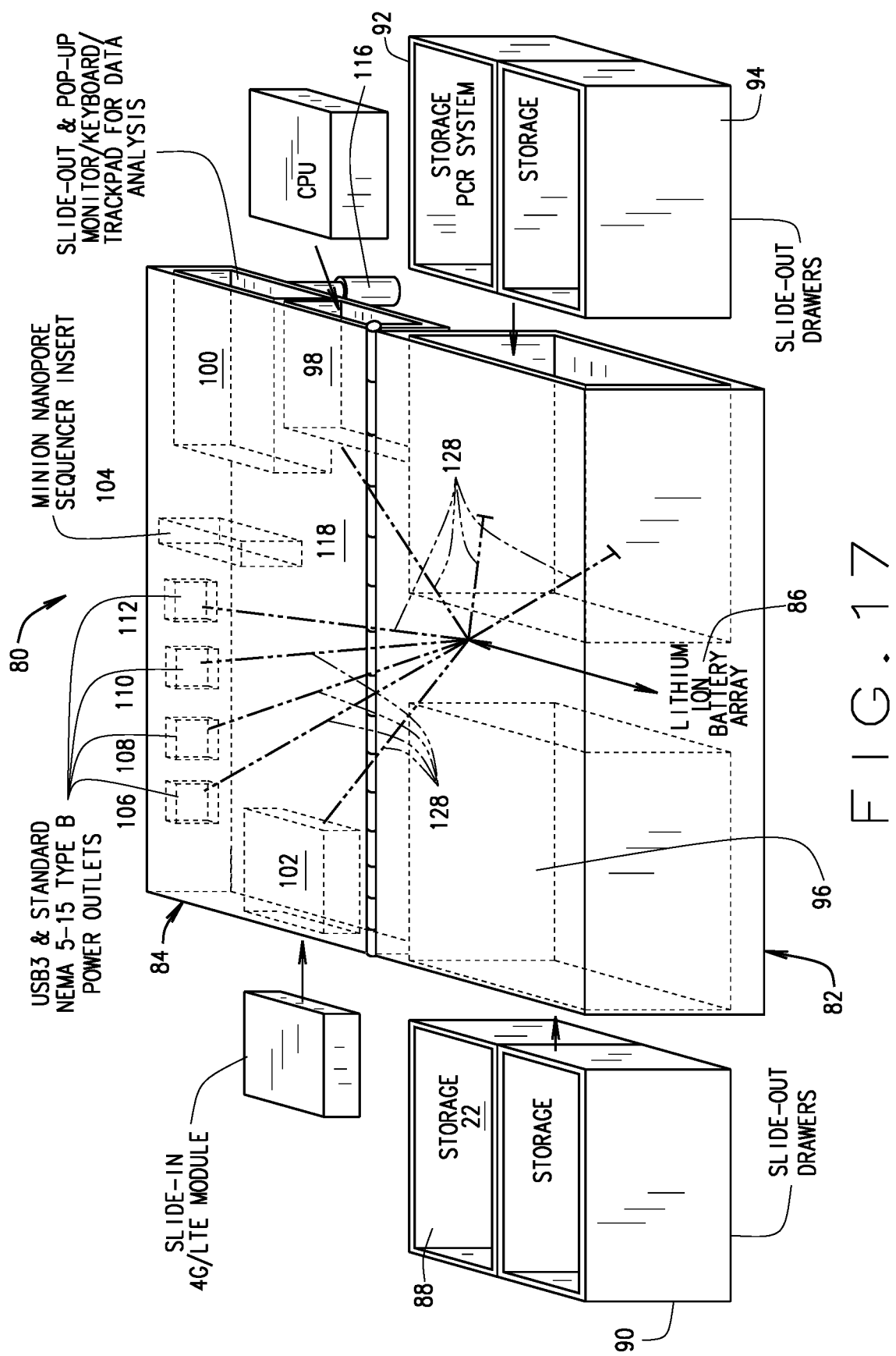

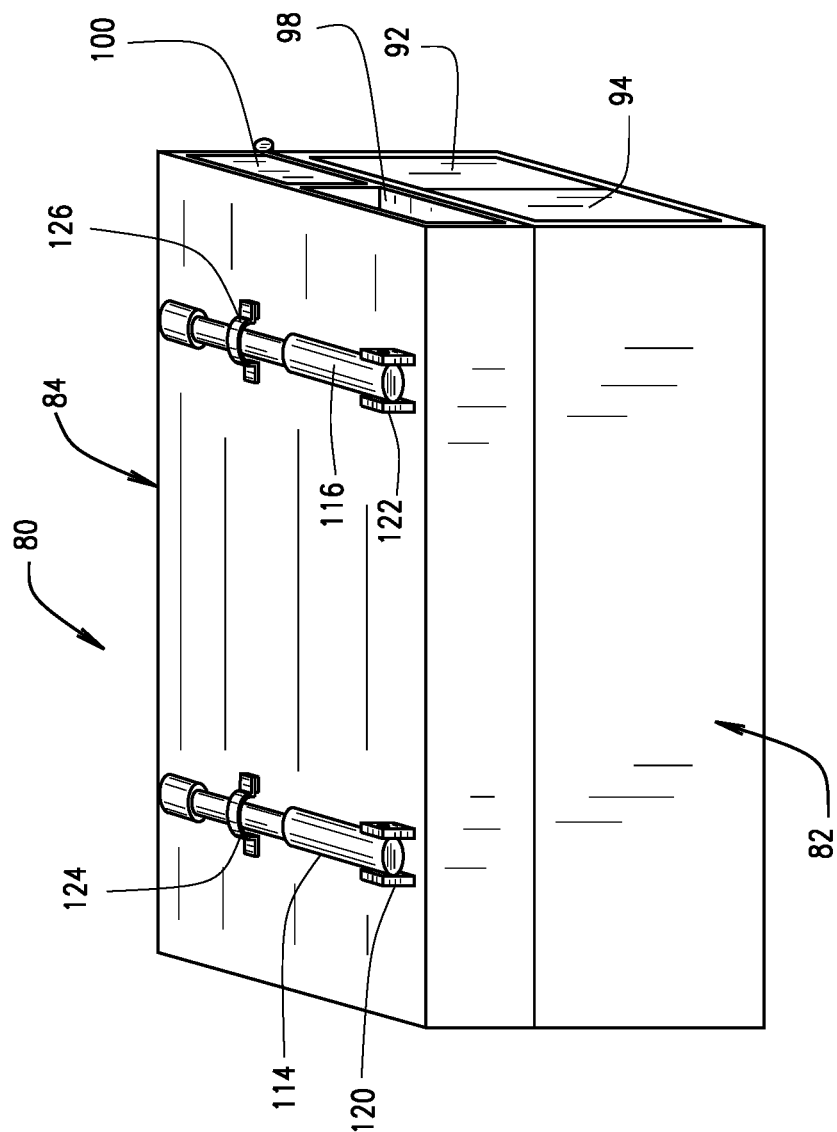

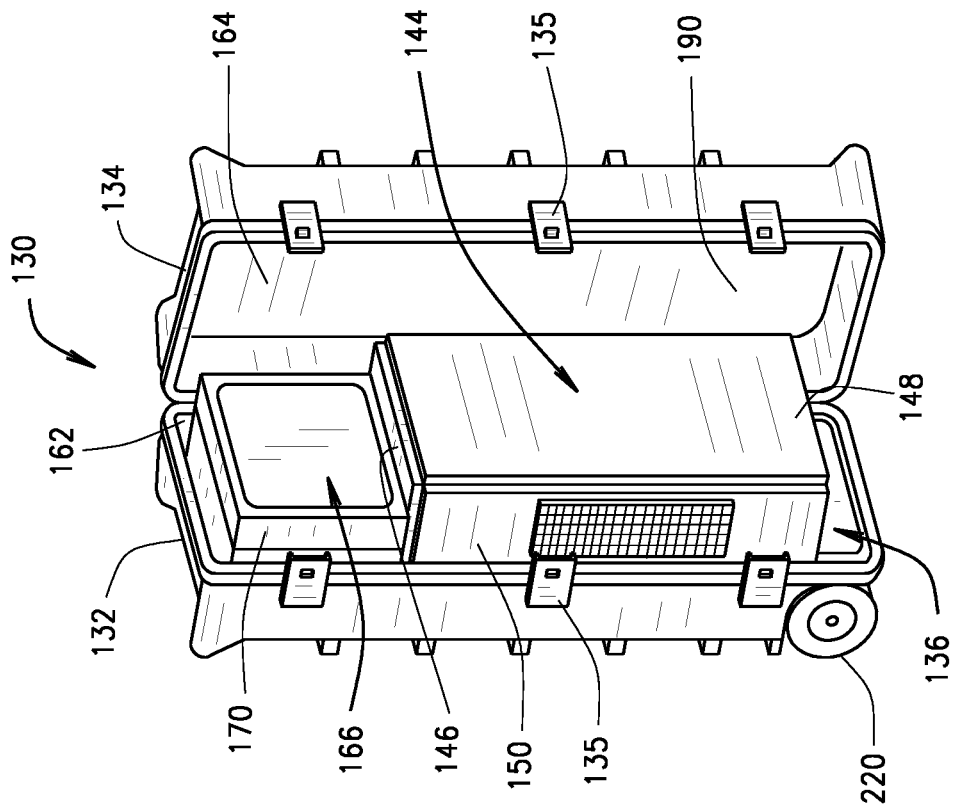
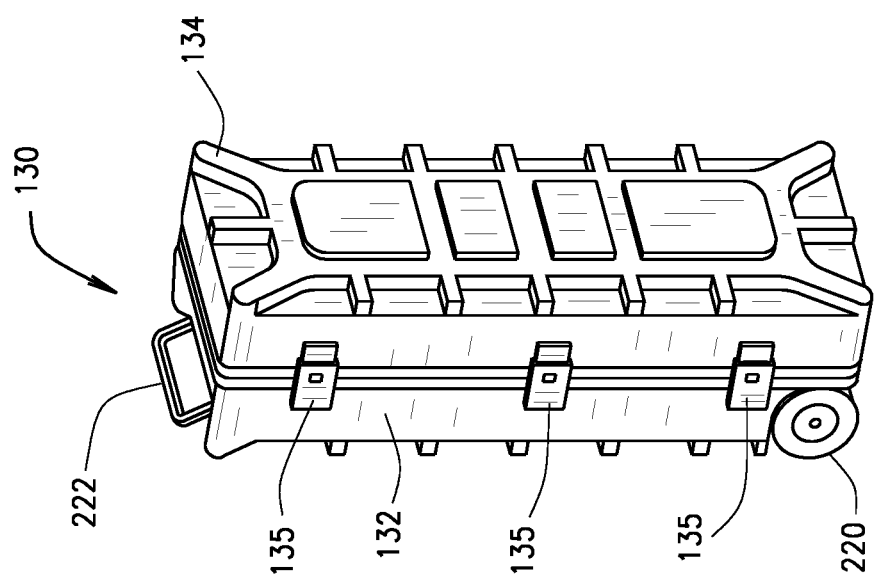

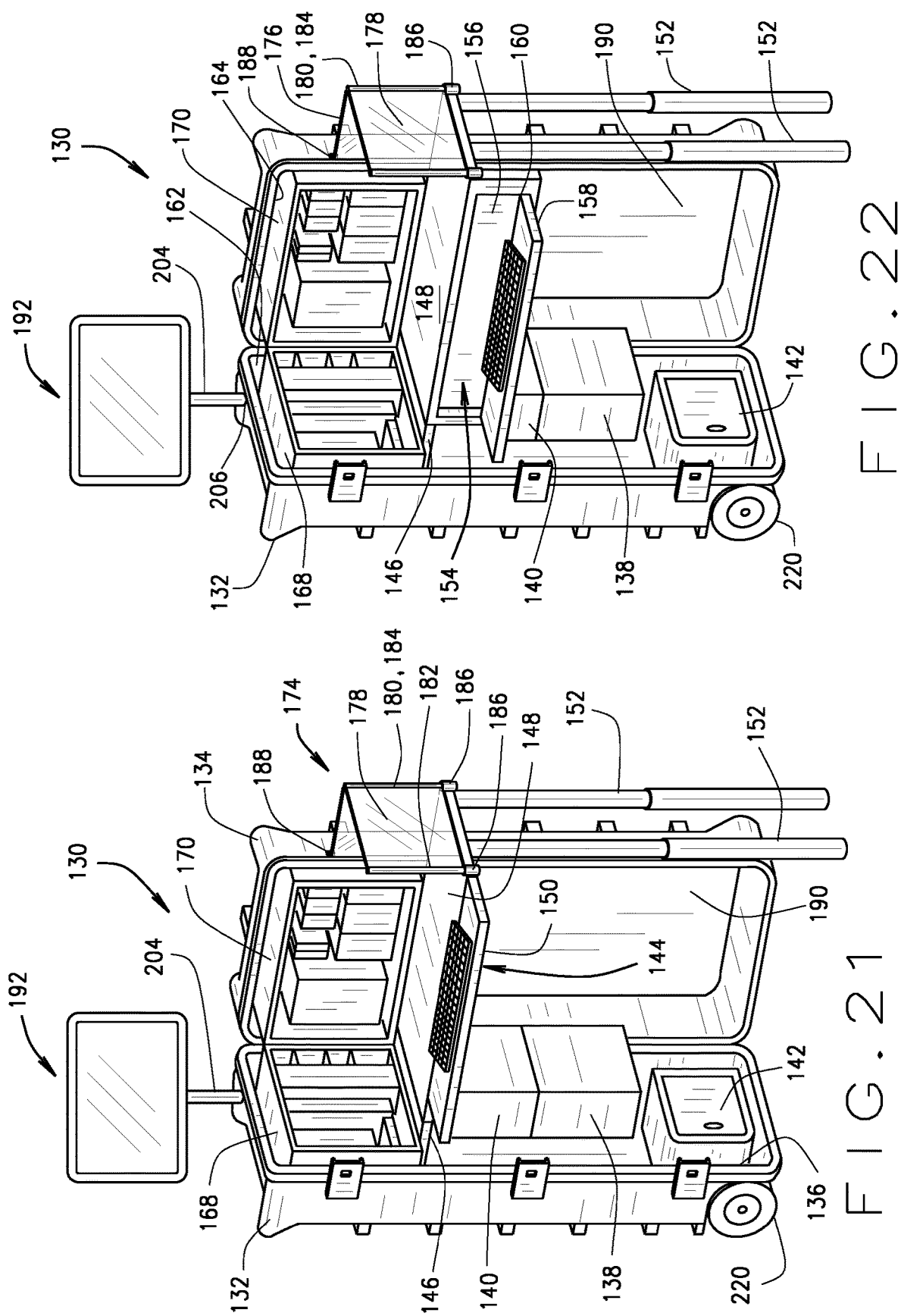

MODULAR MOBILE FIELD-DEPLOYABLE LABORATORY FOR RAPID, ON-SITE DETECTION AND ANALYSIS OF BIOLOGICAL TARGETS

CROSS-REFERENCE TO RELATED APPLICATIONS

This application is a continuation-in-part of U.S. patent application Ser. No. 15/866,073 filed Jan. 9, 2018, the entire disclosure of which is incorporated herein by reference.

BACKGROUND OF INVENTION

The present invention relates generally to a field-deployable system for the detection and sequencing of emerging infectious diseases or other biological targets, and, more particularly, to a modular, mobile molecular detection, sequencing and analysis laboratory which is configured for storage either in a single backpack or in a footlocker type configuration. The present field-deployable backpack/footlocker system enables local, off the grid molecular detection (qPCR), genomic characterization (DNA & RNA sequencing), and bioinformatics analysis and reporting in the field. The present laboratory system includes an integrated cooling compartment and battery array enabling up to 72 hours of continuous use in the field without access to a conventional power supply.

Emerging viruses such as Zika, Dengue, Yellow Fever and Chikungunya to name a few pose eminent threats to the health and economy of the United States and countries in Central America, South America, Africa, and South Asia. Arbovirus surveillance programs typically rely on a process of field collection of mosquitos en masse, separation of mosquitos into pools, followed by detection and characterization of viruses in fixed laboratories. To a lesser extent, sentinel surveillance programs are also leveraged to serve as controlled monitors of virus exposure. The end-to-end process is labor intensive and time consuming, often leading to a lag time of weeks before an accurate assessment of mosquito populations can be made. Furthermore, typically molecular detection of arboviruses from field samples is by conventional quantitative Polymerase chain reaction (qPCR), the gold standard for sample analysis. However, the laboratory equipment needed for qPCR is specialized, expensive to maintain and requires advance training to operate and interpret the resulting data. qPCR alone does not provide essential genomic data critical for tracking emerging pathogens during an ongoing outbreak. New approaches are needed that minimize the obstacles for effective one-health surveillance and that enable real time tracking of emergent pathogens throughout the world.

While portable DNA sequencing, PCR devices, or other molecular detection equipment allow for the characterization of biological samples in the field due to their small footprint, other logistical equipment must also be transported to the field-site to enable the full utilization of the small footprint molecular hardware. For example, current systems typically require the ability to keep reagents and consumables at their respective storage temperatures, typically 4° C. or −20° C., until use during the course of field exercises. Additionally, computational hardware of substantial power, and often times, an Internet connection, is required to run field-forward genomic sequencing devices and to perform the analysis of gigabytes of resulting data. Moreover, various biochemical steps need to be performed to prepare biological samples for molecular detection analyses. A flat, stable workbench area on which to perform these protocols enables optimal sample preparation. Thus, previous field-forward deployments of hand-held/ultra-portable molecular biological detection systems have still required the establishment of a base-of-operations equipped with a stable power source, refrigerators/freezers and/or coolers filled with ice, laptops or desktop computational workstations, folding tables and chairs, and more. Reducing the laboratory footprint of analytical systems to dimensions that could be carried by a single user for operationally relevant time frames has not been accomplished, primarily due to the need for heavy generator-based power required to run cold-chain devices and computational equipment.

It is therefore desirable to develop a field-deployable genomic analysis laboratory that will enable field operators to go from sample to actionable information in the field without the need for an Internet connection or reliable power. Designing a field-deployable system with a forward leaning capability for rapid point-of-need analysis of biological targets from potentially any source, environmental or clinical, is needed to enable rapid detection and characterization of harmful biological agents earlier, as well as accelerate the gathering of actionable field data needed for effective bio surveillance and outbreak response. A modular field-deployable laboratory benchtop and analysis system capable of adapting to multiple technologies as they become available for detecting and sequencing biological agents is a key gap that is limiting the full realization of point-of-need molecular biological detection hardware.

SUMMARY OF INVENTION

A solution that addresses the above challenges would be to break with traditional approaches of bringing the sample to the laboratory. Instead, the present "field-deployable system brings the laboratory to the sample" through the development of several embodiments of a modular, mobile laboratory that provides everything needed for field operators to carry out molecular tests directly in the field. The present system brings together multiple simple-to-use technologies in a flexible, common framework that can be adapted quickly to accommodate new technologies as they emerge. The central focus of the present system is to enable advanced molecular detection and genomic characterization that is mobile and can be operated by trained novices in the field.

One embodiment of the present field-deployable system is a configurable, backpack-based mobile laboratory platform with integrated power supply, cold-storage for frozen and chilled critical reagents, and other necessary components for successfully extracting, amplifying, sequencing, and characterizing biological targets such as specific viruses, pathogens and other bacteria from an environmental or clinical sample. The present system uses customized phase-changed cooling solutions to achieve proper storage temperatures for critical reagents and consumables for up to 72 hours during field deployment, without the need for an external power source. This drastically reduces the power requirements for the laboratory footprint as a whole, allowing the use of multiple Li-ION or similar batteries to provide the required power. The present system also includes a solid-state computing system for local analytical needs (for example, bioinformatics), and additional ancillary equipment such as a small centrifuge, sample bead-beating/lysis systems, or thermal cyclers. The present system is designed for achieving the first true "backpack laboratory" and is intended for field use in ruggedized environments.

The solid-state computing system, such as an Intel NUC system with quad-core i7 2.6 GHz processors and 32 GB RAM, is used for local data processing and draws under 60 watts of power at peak load and less than 7 watts when idol. When equipped for Nanopore sequencing, integrated batteries in the present system can power the computational and analytical hardware for 72 hours of nominal usage.

2. Rapid PCR-based detection/quantification of target nucleic acids using a system such as the Biomeme two3 qPCR system;

3. Direct sequencing of either amplicon or whole-sample DNA/RNA using a system such as the Oxford Nanopore MinION system;

4. Local data storage and bioinformatics analysis of sequencing data using a bioinformatics pipeline;

5. A cooling compartment for critical lab reagents and/or samples;

6. A Li-ION battery powered source enabling the present mobile laboratory to operate for at least 72 hours.

The present system will be encapsulated in an expedition-style backpack with a hard inner shell suitable for a single operator to carry, unpack, and carry out end-to-end analysis in the field.

An overview of some of the relevant technologies and capabilities of the present system are identified in the chart below.

| Technology | Suggested Platform | Applications |
| --- | --- | --- |
| qPCR | Biomeme Two3system | Targeted detection of pathogens directly from clinical and environmental samples. |
| DNA/RNA Sequencing | Oxford Nanopore MinION | Re-sequencing of targeted amplicons produced by qPCR; Direct metagenomics (unbiased) sequencing of samples where qPCR fails to detect pathogens of interest |
| Computing & Analysis | MRIGlobal hardened solid-state computing platform with analysis pipeline | Automated, direct analysis of qPCR results produced by Biomeme two3system Automated bioinformatics analysis of MinION data using custom sequence analysis pipeline or the like. Rapid reporting and uploading of result to cloud based dashboard system Monitoring of cooling system conditions and power reserves. |
| Cooling System | MRIGlobal hardened cooling system | Maintaining critical cold reagents at 4° C. for up to 72 h Storing priority samples after collection |

When fully loaded, the present backpack system weighs less than 30 KG, manageable by a single operator. Using rapidly customizable Velcro® inserts or dividers, the present backpack can readily accept sensitive, portable chemical and biological analysis equipment and associated consumables for transport and efficient use in field settings. The present system can provide all necessary hardware, reagents, and consumables to collect the biological sample, extract nucleic acids, prepare Nanopore-ready sequencing libraries, and sequence and analyze resulting data. The present backpack includes an integrated workbench which provides a stable work station in varied terrain. The present system is designed for use in field-forward operational biosurveillance and epidemiology settings, and leverages ultra-portable molecular biology hardware, for example, the Biomeme two3 PCR system, Oxford Nanopore MinION system, and a robust computing platform for rapid local bioinformatics analysis.

Although the specific systems included within the present system could be altered to meet end-user requirements, the present field-deployable backpack system will include and integrate at least the following systems:

1. Reagents and consumables for extraction and purification of nucleic acids from environmental or clinical samples;

The present field-deployable system can be custom-designed for specific missions and/or specific targets and will carry the specific ancillary equipment to achieve the designated mission and/or targets.

Another embodiment of the present system will be encapsulated in a hardened heavy-duty outer backpack shell having a wide variety of different storage compartments for holding and storing all of the necessary components referenced above including a cold storage compartment, a deployable workbench, and a supporting leg system which can be deployed to support the entire laboratory.

Still further, another embodiment of the present system will be encapsulated into a footlocker configuration having the same components and capabilities referenced above.

Other aspects and advantages of the present invention will become apparent to those skilled in the art from the following detailed description of the various embodiments and the accompanying drawings.

BRIEF DESCRIPTION OF DRAWINGS

For a better understanding of the present invention, reference may be made to the accompanying drawings.

FIG. 17 is a perspective view of still another embodiment of the present field-deployable laboratory in a footlocker configuration constructed according to the teachings of the present invention.

FIG. 18 is a perspective view of the footlocker laboratory of FIG. 17 shown in its packed or closed condition.

FIG. 19 is a perspective view of still another embodiment of the present field-deployable footlocker configured laboratory constructed according to the teachings of the present invention.

FIG. 20 is a perspective view of the field-deployable footlocker laboratory of FIG. 19 shown in a partially unpacked configuration.

FIG. 21 is a perspective view of the field-deployable footlocker laboratory of FIGS. 19 and 20 shown in its fully deployed configuration.

FIG. 22 is a perspective view similar to FIG. 21 illustrating another embodiment of the keyboard tabletop portion of the deployed workbench station.

FIG. 23 is an exploded perspective view similar to FIG. 20 showing the mobile backpack member removed from the field-deployable laboratory.

FIG. 24 is a perspective view showing the mobile backpack member deployed for field use by a user.

FIG. 25 is a perspective view of still another embodiment of the present field-deployable footlocker laboratory showing use of a single adjustable leg member for supporting the workbench station.

FIG. 26 is a rear elevational view of the computer monitor structure associated with the present field-deployable footlocker laboratory housing various computer components with the rear cover member removed.

FIG. 27 is an exploded perspective view of the computer monitor structure of FIG. 26.

FIG. 28 is a partial perspective view of the mobile field-deployable footlocker laboratory showing the positioning and location of a power strip associated with the laboratory.

DETAILED DESCRIPTION OF THE INVENTION

Referring to the drawings more particularly by reference number wherein like numerals refer to like parts, FIG. 1 illustrates one embodiment of an expedition-style backpack system 10 that is specifically designed to hold each of the required components for accomplishing the detection, amplification, sequencing and analysis of various specific viruses, pathogens, bacteria and other infectious diseases accumulated in the field. The backpack system 10 is a turn-key modular diagnostic laboratory capable of supporting devices for a wide variety of different applications including, but not limited to, point-of-care diagnostics, mobile DNA sequencing, field forensics, environmental monitoring, disease surveillance, and more. The present backpack 10, as will be explained further in detail, includes a plurality of different compartments capable of housing and storing a battery pack array 24 for providing power for at least 72 hours of continuous use, an integrated cooler and freezer system 22, an ultra-mini centrifuge 18, computing and analysis equipment including a local Wi-Fi hotspot, a laptop, storage for a variety of POC devices, a mobile bioinformatics analysis system 26, a PCR system 30, a DNA sequencing system 32, a benchtop workspace 20, pipettes 12, assorted cables, tubes, tips, dry and wet reagents 14, and all other materials necessary for field testing samples taken in the field and for accomplishing the electronic communication between the relevant components.

As best illustrated in FIG. 2, the present backpack 10 will, at a minimum, include various compartments, pouches and other access areas for storing the various components identified in FIG. 2 including storage locations for pipettes and pipette tip boxes 12, storage locations for non-temperature sensitive bottled reagents 14, storage location for a sample tube rack 16, storage location for a mini centrifuge 18, a workbench 20, storage location for phase-change coolants 22, storage location for an appropriate battery array 24, storage location for a mobile bioinformatics analysis system 26 such as the Intel NUC device, appropriate power connections 28 for the bioinformatics analysis system 26 and the mini-centrifuge 18, storage location for the PCR system 30, and a storage location for the DNA/RNA sequencing system 32. It is recognized and anticipated that the backpack 10 may be configured differently than as illustrated in FIG. 2 so long as the necessary equipment as outlined in FIG. 2 can be stored therein in a packed configuration as illustrated in FIG. 1. Other embodiments of the present backpack 10 will be discussed in more detail hereinafter.

Figure 1:
FIG. 1 is a perspective view of one embodiment of the present field-deployable backpack constructed according to the teachings of the present invention.

The present backpack 10 can likewise be a custom-designed, 3D-printed, heavy duty plastic mold for secure transportation and storage of all necessary materials. This embodiment will be discussed later with respect to FIGS. 7-14. In addition, a 3D printed plastic base plate may likewise be fitted into a custom pack to provide extra support. Rapid PCR-based detection/quantification of target nucleic acids can be accomplished using the Biomeme Two3 qPCR system 30, although other PCR systems may likewise be utilized to target detection of specific viruses, pathogens and bacteria. The Biomeme Two3 system is currently available in the marketplace and can run up to 8 tests on a single charge. The DNA sequencing system 32 can be the Oxford Nanopore MinIon Mk1 system which is a hand-held next generation system which is simple to use and produces rapid turnaround time, less than 3 hours, for direct sequencing of either amplicon or whole-sample DNA/RNA. Here again, other equivalent or comparable DNA/RNA sequencing systems can likewise be used in the present system. The mobile bioinformatics analysis system 26 can be the Intel NUC system which is an ultra-compact, cloud-enabled mobile system which provides local data storage and bioinformatics analysis of sequencing data using a custom bioinformatics pipeline. This solid-state computing platform, which acts as a headless server for bioinformatics analysis and operation of the Nanopore sequence system, produces rapid reporting and uploading of results to cloud based dashboard systems and can likewise monitor cooling system conditions in the cooling compartment and power reserves as will be hereinafter explained. This system will be capable of analyzing the Oxford Nanopore Minion data in the absence of an internet connection and carries the latest generation of Intel processors and is configured up to 2 TB of storage and 32 GB of RAM allowing rapid, complex phylogeny and genomic characterization of pathogens and other biological select agents and toxins.

The Intel NUC computing platform likewise enables several capabilities not currently available in field-forward molecular detection and diagnostic systems, namely, (1) re-sequencing of amplicons for phylogenetic analysis, (2) detection of pathogens not covered by target assays, and (3) functional characterization of genome-based virulence factors, toxin genes, and antimicrobial resistance markers. In addition, the system will likewise run software for operating the PCR system 30 and the system will comprise a solid-state compact single-board computing system with sufficient storage and compute power to run all the analytical pipelines. The compartments housing the computing platform 26, 30 and 32 will be padded storage compartments.

The battery array 24 can include one or more Li-ION batteries to provide the required power. For example, the battery array could include a military-grade UB12590 set of batteries having a rugged case construction with high energy density (144 Wh/Kg), an operating temperature range between −32° C. to 60° C., and a weight of 1,440 g. It is likewise recognized and anticipated that other battery arrays can likewise be utilized to accomplish the present application.

In addition, the present backpack 10 will include a dedicated hardened cooling compartment for housing the phase-change cooling system 22. The cooling compartment can be segregated into two compartments, one to hold critical lab reagents at 4° C., and one to hold lab reagents at −20° C. These same compartments can also be used to hold and store priority samples after collection requiring cold storage. Maintaining critical cold reagents and samples at 4° C. and/or −20° C. for up to 72 hours is accomplished through the use of phase-change proprietary liquid mixtures. As best illustrated in the phase-change graph illustrated in FIG. 3, solid to liquid phase change of proprietary liquid mixtures keeps the material housed within the cooling compartments at a constant fixed temperature until the phase change is complete. No power input is required to hold the temperature constant.

Figure 3:
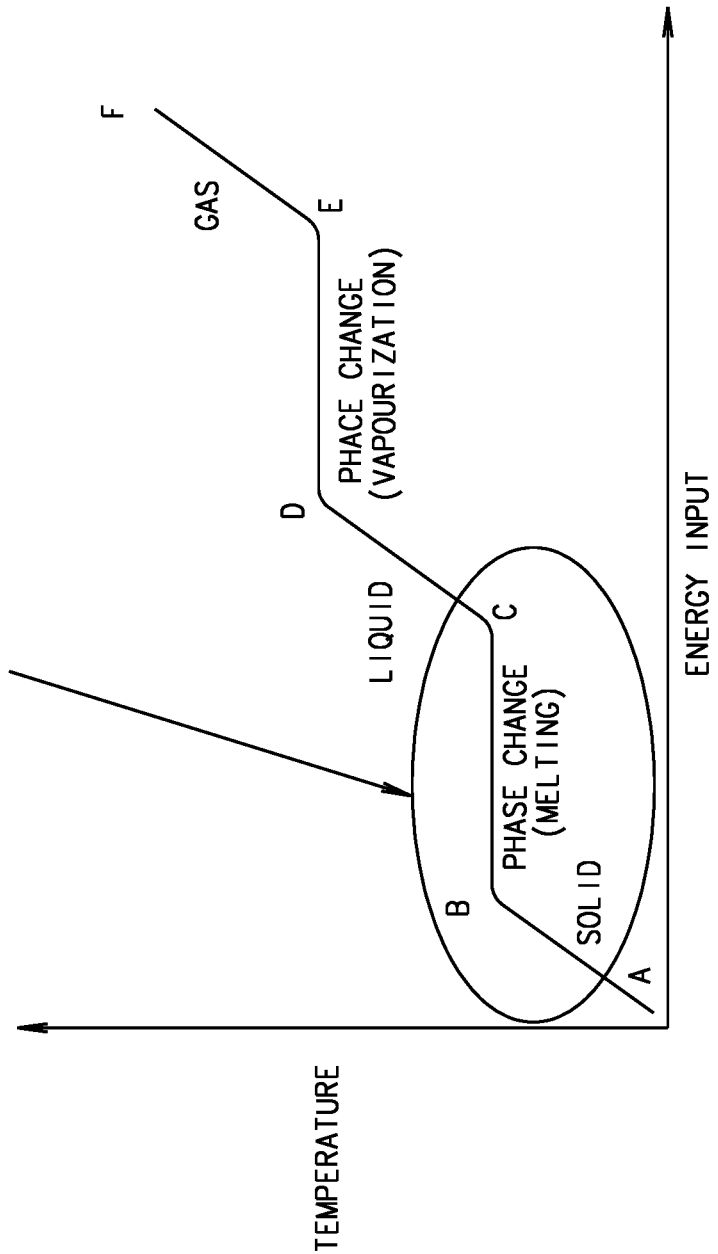
FIG. 3 is a graph representing the phase-change cooling associated with the proprietary liquid mixture used in association with the cooling compartments associated with the backpack of FIG. 1.

FIG. 3 represents the phase-change curve of a proprietary liquid mixture. It illustrates the phases that the proprietary material goes through during its transition from a solid to a liquid to a gas. The plateaus on the graph illustrated in FIG. 3, namely, the plateau B-C and the plateau D-E, represent the proprietary material staying at a certain constant temperature until all of the material is converted to the next phase. Since it takes 72 hours for the proprietary material in the present cooling chambers to melt from a frozen solid to completely liquid, the proprietary material will stay at a pre-determined desired selected temperature for that period of time, keeping the reagents and samples either chilled or frozen depending upon which compartment they are housed in. The 72 hours includes the time illustrated in FIG. 3 from A to C on the graph. When the present backpack 10 is about to be deployed to the field, the operator will remove the phase-change material from a refrigerator and/or freezer and will place the material in its appropriate cooling compartment. A different proprietary material is used for each different selected temperature. As soon as the proprietary material is removed from the refrigerator/freezer, it will begin to warm up from point A to point B in FIG. 3 until it reaches its melting temperature. The phase-change material will then stay at its melting temperature until all of the material has melted, that is, from point B to point C in FIG. 3. The total time from point A to point C equals approximately 72 hours. Depending upon the type of proprietary liquid mixture selected, different temperatures can be maintained within the various cooling compartments during a 72 hour operational period. With phase-change cooling and the appropriate battery array, the present backpack can be operated effectively for 72 hours before requiring re-charging of the batteries and re-freezing of the phase-change material.

Figure 2:
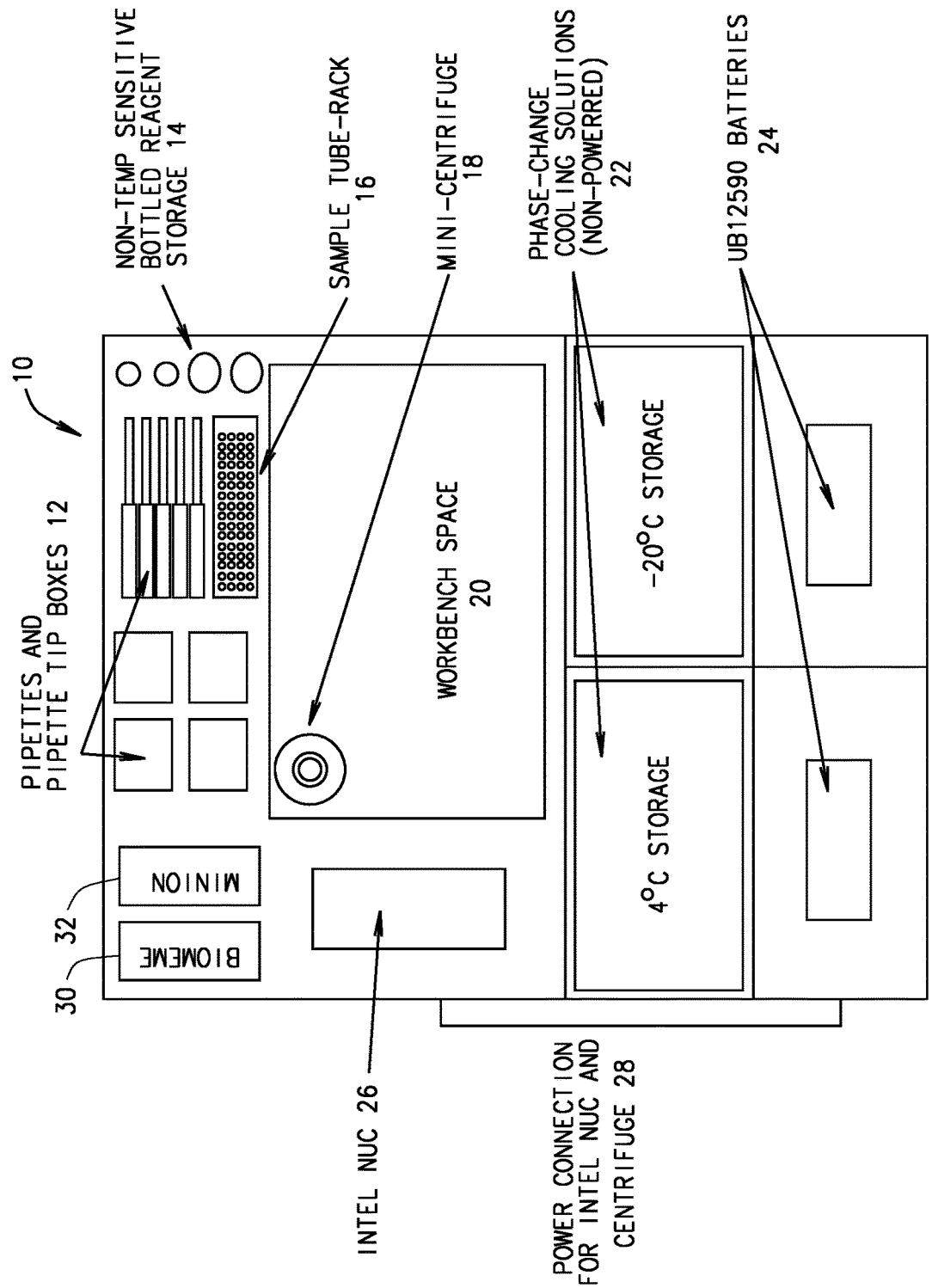
FIG. 2 is a schematic presentation of at least some of the various compartments and at least some of the various components associated with the backpack of FIG. 1.
Figure 4:
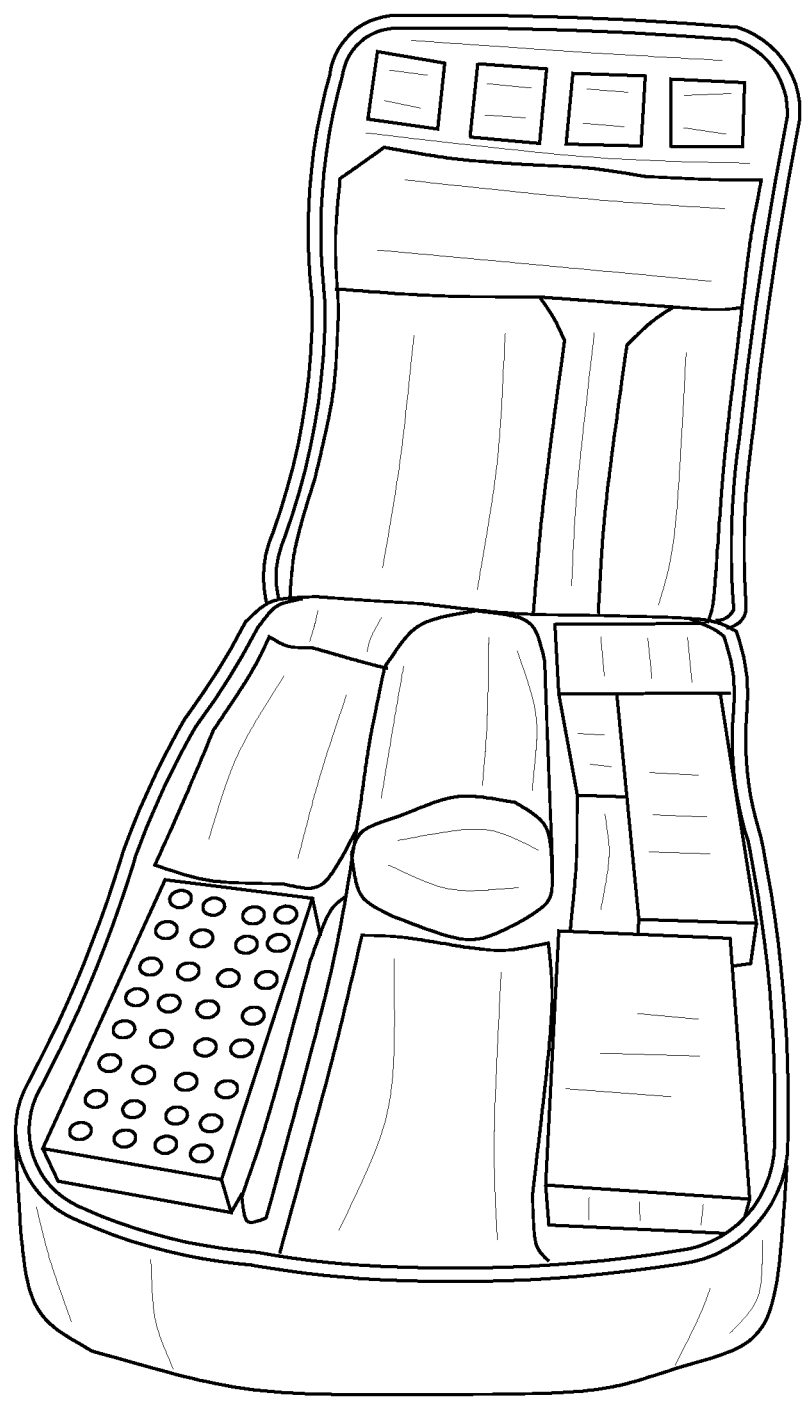
FIG. 4 is a perspective view of one embodiment of the present backpack of FIG. 1 showing various components housed within the present backpack in a packed condition.

FIG. 4 illustrates one embodiment of a packed backpack 10 including all of the required components as illustrated in FIG. 2 and discussed above. Using rapidly customizable Velcro-type inserts and/or dividers, the present backpack 10 can readily accept sensitive, portable analysis equipment with associated consumables for transport and efficient use in the field. These divider members can be easily moved and reconfigured to accommodate the necessary equipment housed within the present backpack 10.

Figure 5:
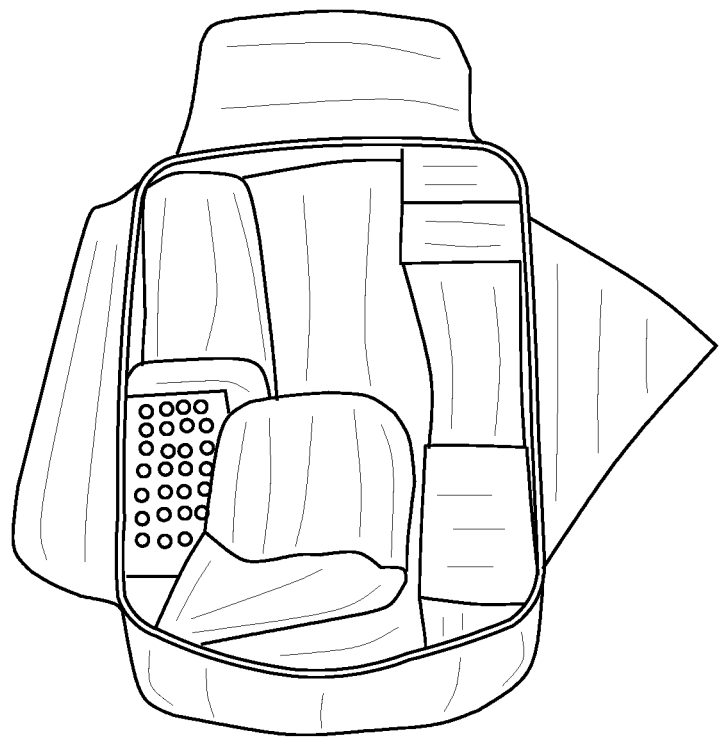
FIG. 5 is a perspective view of another embodiment of the present backpack of FIG. 1 showing various components housed within the present backpack in another packed condition.

FIG. 5 illustrates another embodiment of the packed backpack 10 configured for another application. In this regard, depending upon the particular application, such as water safety testing, food safety testing, environmental biosurveillance, clinical/bed-side diagnostics, forensics and other applications, the present backpack 10 can be reconfigured to carry the necessary equipment for targeting specific pathogens and other biological select agents and toxins.

Figure 6:
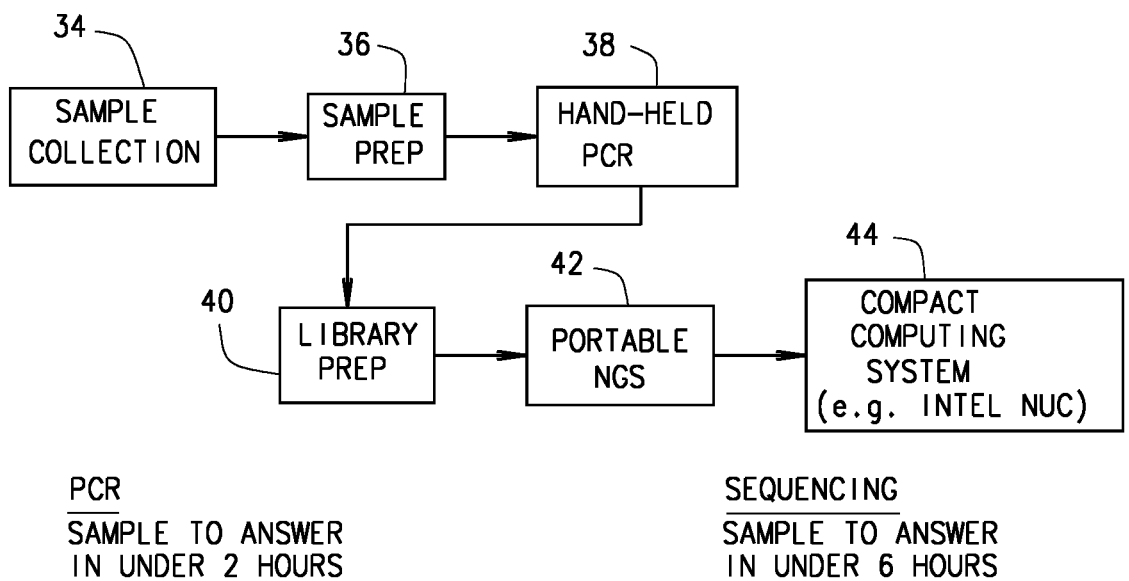
FIG. 6 is a schematic flowchart showing one embodiment of the protocol used for collecting a targeted sample and using the various components stored within the present backpack of FIG. 1 to extract, amplify, sequence and characterize the targeted sample and obtain the bioinformatics data analysis.
Figure 7:
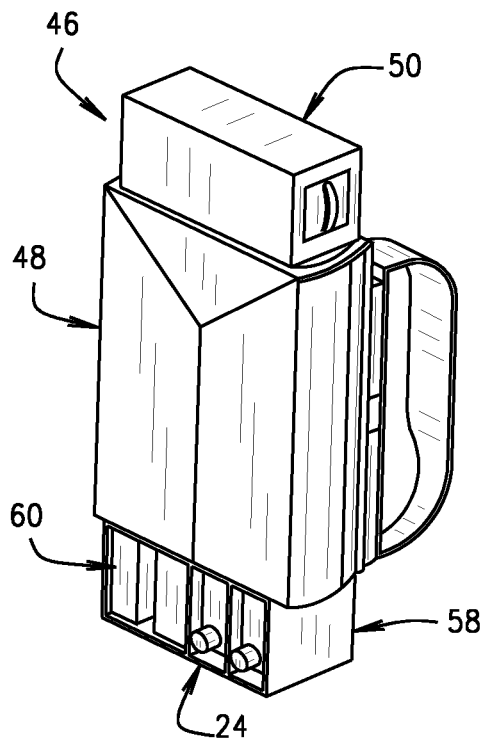
FIG. 7 is a front perspective view of another embodiment of the present field-deployable backpack constructed according to the teachings of the present invention.
Figure 8:
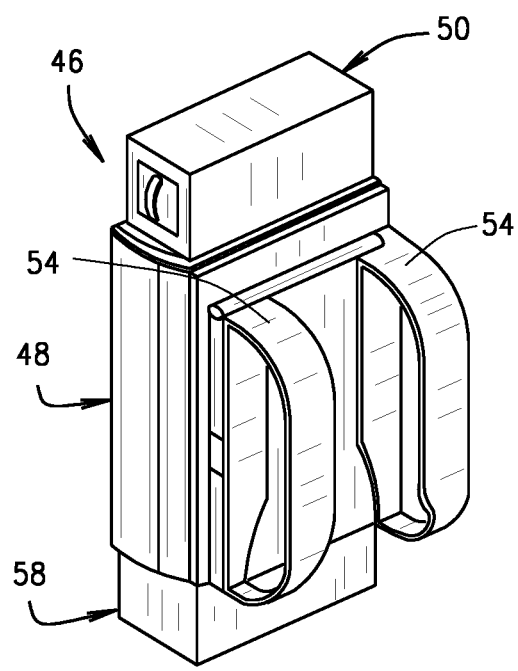
FIG. 8 is a rear perspective view of the backpack of FIG. 7.

FIG. 6 is a representative flow chart illustrating one protocol for using the present backpack 10 in the field. Once an operator arrives at the specific field location, traps or other methods are typically set up and/or used for initial capture of the particular pathogen, virus and/or bacteria targeted at step 34 in FIG. 6. This could include blood samples, forensic swabs, soil water plant or animal tissue.

Once the targeted samples are collected, extraction and purification of the targeted pathogens from the samples is accomplished at step 36 using known methods. Once extraction and purification is accomplished, the hand-held PCR unit is used at step 38 to detect and quantify the target pathogen. Once the targeted pathogens are detected and quantified, a series of chemical steps (library prep) are performed at step 40 to ready the extracted nucleic acids for sequencing on the portable NGS (next generation sequencing) device such as the Oxford Nanopore Minion sequencing unit which takes place at step 42. Once step 42 is accomplished, the compact computing system 26 runs the analysis at step 44 as explained above. The present system 10 is designed to identify the specific virus, pathogen and/or bacteria targeted within two hours and identification of the specific virus, pathogen and/or bacteria genetic sequence can be accomplished within six hours. These times may vary depending upon the particular equipment utilized and the specific targeted virus, pathogen and/or bacteria.

Figure 10:
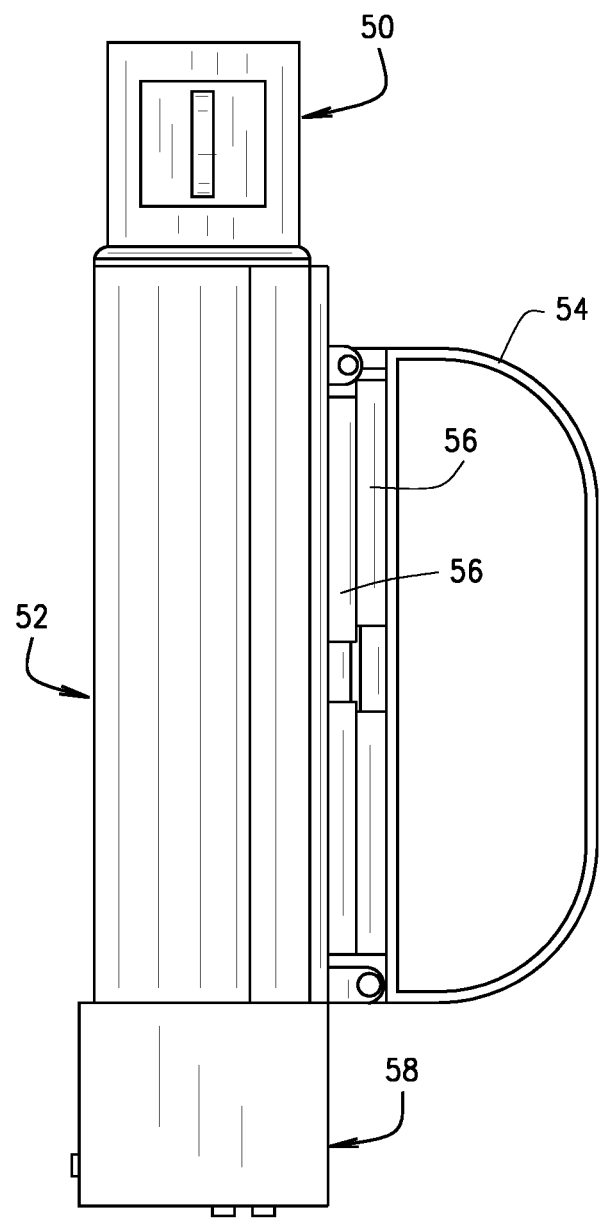
FIG. 10 is a side elevational view of the backpack of FIGS. 7-9.
Figure 9:
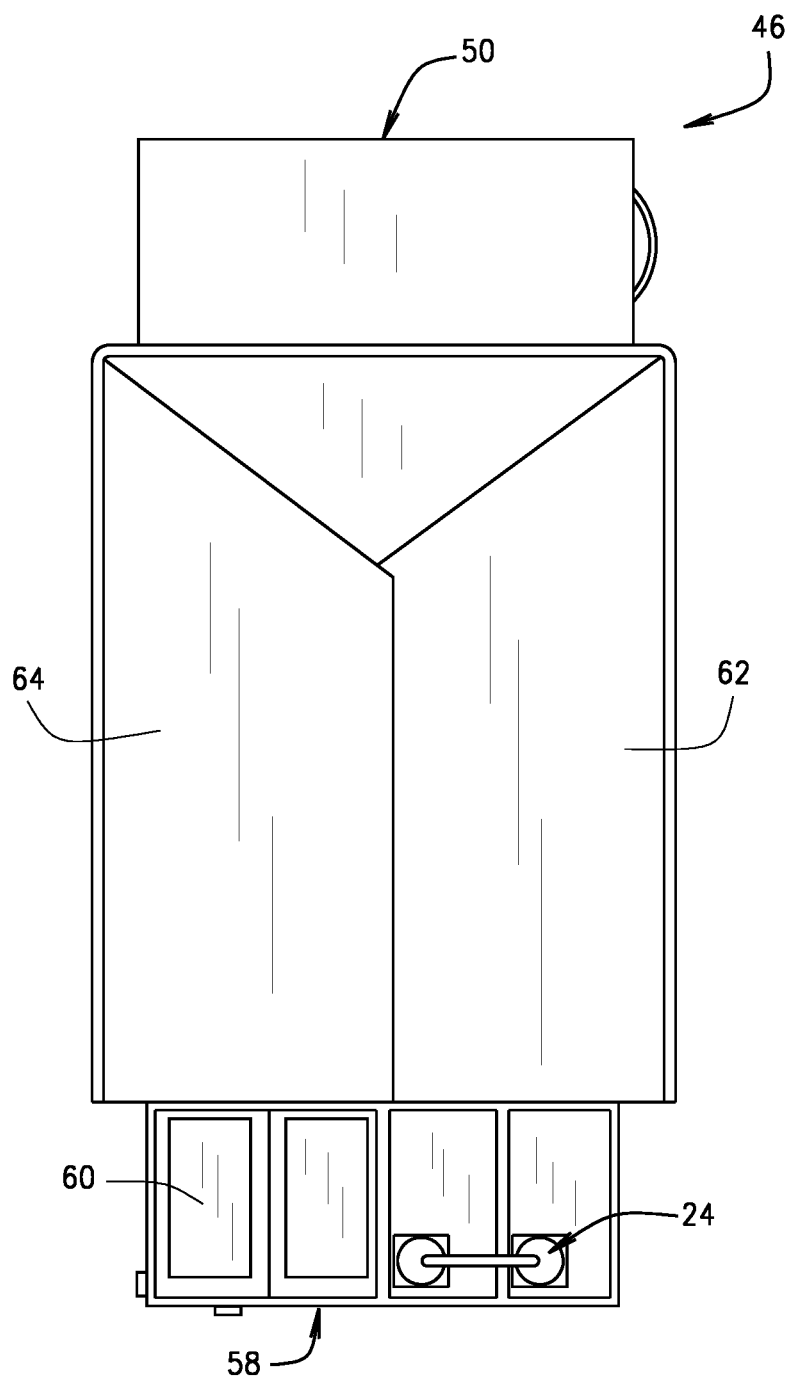
FIG. 9 is a front elevational view of the backpack of FIGS. 7 and 8.
Figure 11:
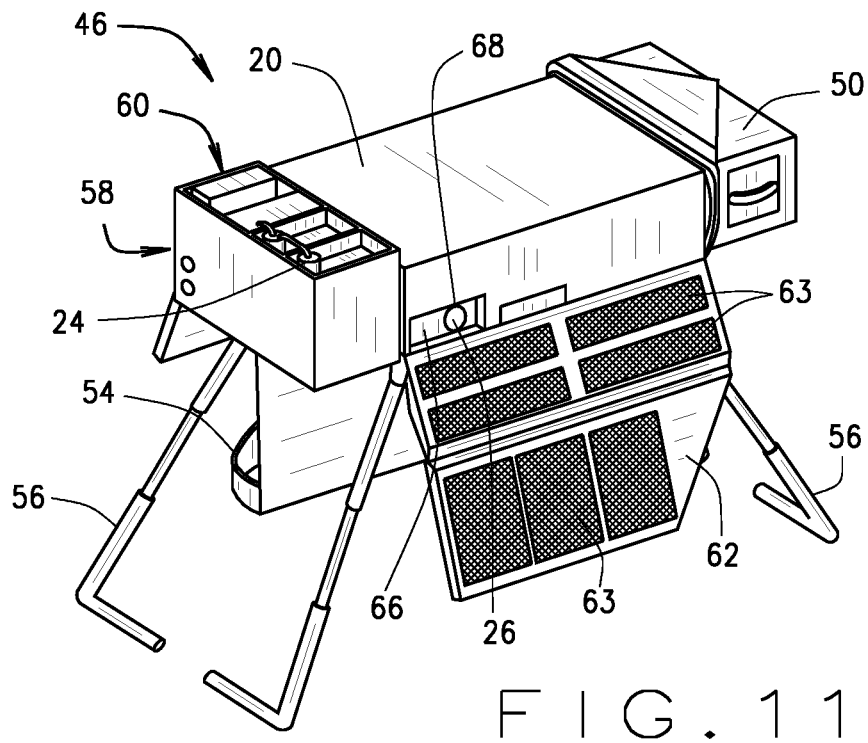
FIG. 11 is a right side perspective view of the backpack of FIGS. 7-10 shown in its deployed or unpacked configuration.
Figure 12:
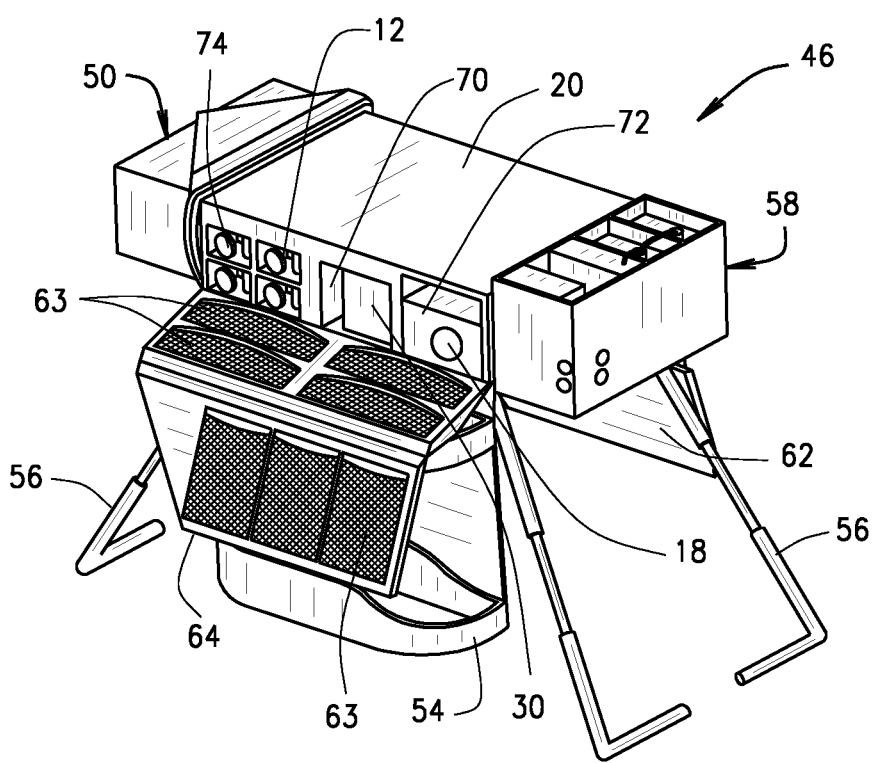
FIG. 12 is a left side perspective view of the backpack of FIGS. 7-10 shown in its deployed or unpacked configuration.

FIGS. 7-14 illustrate still another embodiment 46 of the present field-deployable backpack wherein FIGS. 7-10 illustrate the backpack 46 in its packed configuration and FIGS. 11-14 illustrate the backpack 46 in its unpacked or deployed configuration. As best illustrated in FIGS. 7-10, the present backpacks 46 includes a hardened heavy-duty outer shell 48 which can be made from a plastic molded material, a 3D printing process, or other manufacturing process for providing secure transportation and storage of all of the necessary equipment stored therewithin. The backpack 46 includes an upper storage compartment 50 which is specifically designed for housing the cooling/freezer components of the present system such as the phase-change cooling system 22 previously described, a middle section 52 which houses the PCR detection system 30, the DNA/RNA sequencing system 32, the computing and analysis platform 26, the mini-centrifuge 18, the workbench 20, and all of the necessary ancillary equipment including pipettes 12, reagent bottles 14, tube racks such as tube rack 16, and other equipment and storage compartments. The center section 52 likewise includes a pair of adjustable strap members 54 for allowing a single user to carry the entire backpack 46 as well as a pair of folding and extendable leg members 56 as best illustrated in FIGS. 11 and 12. The leg members 56 support the workbench area 20 and the other compartments associated with the backpack 46 when the backpack 46 is in its unpacked configuration as best illustrated in FIGS. 11 and 12. The leg members 56 can be telescoping in nature or their adjustability can be accomplished using other known methods. It is important that the leg members 56 fold into a tight small configuration as best illustrated in FIG. 10 when backpack 46 is in its packed condition.

The backpack 46 likewise includes a lower compartment 58 which houses the battery array 24 and power converters 60 for converting power from the batteries to the appropriate detection, sequencing and data analysis equipment housed within the backpack 46.

FIGS. 11 and 12 illustrate the present backpack 46 in its unpacked or deployed configuration with leg members 56 pivotally rotated and extended so as to support the entire backpack laboratory including the workbench area 20, upper and lower compartments 50 and 58, and side panels 62 and 64. FIG. 11 illustrates a right side perspective view of the present backpack 46 in its deployed or unpacked configuration showing compartments 50 and 58 positioned adjacent to the workbench area 20 in a substantially horizontal platform with leg members 56 extended and deployed. Upper compartment 50 can be segregated into two separate cooling compartments for holding sequencing reagents and other proper clinical/forensic samples at two separate stored temperatures such as at 4° C. and at a −20° C. Two separate proprietary liquid mixtures, one for each segregated compartment in compartment 50, can be utilized to maintain the two separate storage temperatures. It is also recognized and anticipated that other temperatures could likewise be maintained within the cooling compartments 50 depending upon the particular application and the targeted pathogens.

Lower compartment 58 is also shown in its deployed condition housing battery array 24 and power converters 60. A compartment 66 is located on the right side of the deployed backpack 46 (FIG. 11) for housing the computing and analysis platform 26 such as the Intel NUC platform and server access is provided to compartment 66 via the opening 68 on the right side of the deployed backpack as best illustrated in FIG. 11.

FIG. 12 is a perspective left side perspective view of the deployed or unpacked backpack 46 showing a plurality of compartments for housing other equipment. For example, compartment 70 houses the PCR detection system 30 such as the Biomeme two3 system; compartment 72 houses the mini centrifuge 18; and compartment 74 houses reagent bottles 14. As best illustrated in FIGS. 11 and 12, the side panel or side shroud 62 includes a plurality of Velcro® attachment means 63 for re-positioning the side panel 62 back into its packed configuration as best illustrated in FIGS. 7-10. Side panel 64 likewise includes a plurality of similar Velcro® attachment means 63. It is also recognized and anticipated that side panels 62 and 64 can likewise be opened and closed using zippers or other comparable attachment mechanisms. In this regard, each side panel 62 and 64 is selectively movable between a first position wherein each panel covers at least a portion of the middle section 52 when the backpack member 46 is in its packed configuration, and a second position providing access to the middle section 52.

Figure 13:
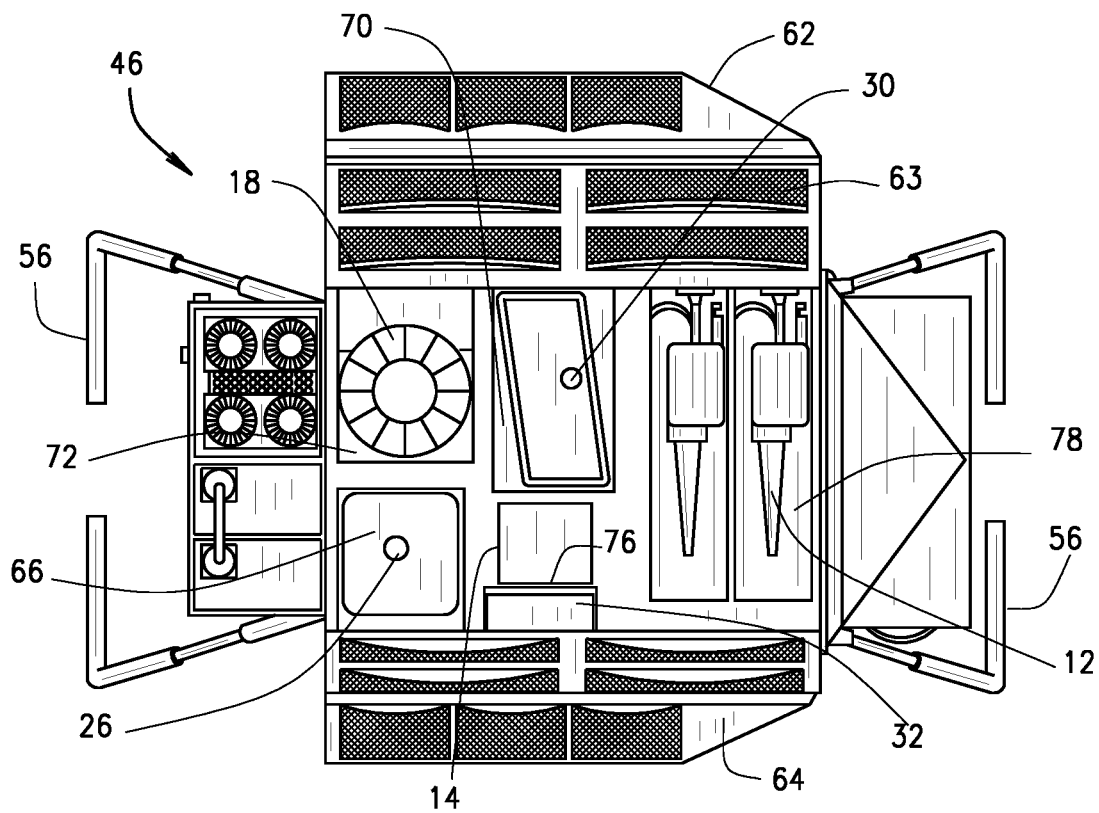
FIG. 13 is a top plan view of the backpack of FIGS. 7-12 shown in its deployed or unpacked configuration with the workbench area removed for internal viewing of the various compartments associated therewith.
Figure 14:
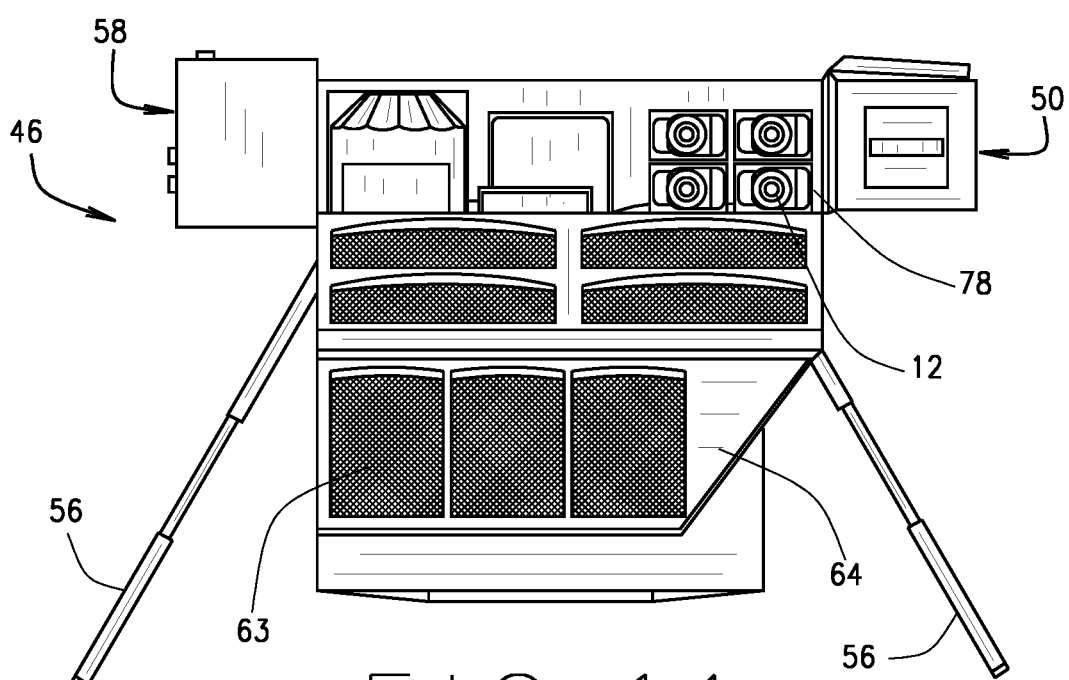
FIG. 14 is a right side elevational view of the backpack of FIG. 13.

FIGS. 13 and 14 illustrate the present backpack 46 and its unpacked or deployed configuration with the workbench area 20 removed so as to view the internal compartments housed underneath workbench 20. As clearly shown in FIG. 13, the computing and analysis platform 26 is housed within compartment 66; mini centrifuge 18 is housed within compartment 72; the PCR system 30 such as the Biomeme two3 system is housed within compartment 70; the DNA/RNA sequencing system 32 such as the Oxford Nanopore MinIon system is housed within compartment 76; and the pipettes 12 are housed within compartment 78. The laptop can be stored in external pouches (not shown) which are located on the outside portion of the side panels 62 and 64. Other external storage pockets or compartments can likewise be located along the exterior of the present backpack 46. It is recognized and anticipated that all of the various components discussed above can be housed in different compartments and that the various compartments can be moved and repositioned to other locations within the central section 52, or the components can be housed in external pouches positioned and re-located on the exterior of the backpack 46. Other configurations of the backpack 46 are likewise envisioned and anticipated so long as the backpack is deployable in its unpacked configuration so as to provide a substantially horizontal workbench area or surface such as workbench area 20 for operational use in the field. It is also recognized and anticipated that the upper cooling compartments 50 and the lower compartment 58 can likewise be re-located or repositioned, and it is envisioned that such compartments can be likewise housed within the center section 52. Other configurations of backpacks 10 and 46 are likewise anticipated and envisioned for future use.

Regardless of the specific configuration and location of the various compartments for housing the various required equipment and ancillary materials, it is important that the present backpack either include a workbench area such as workbench area 20, or that the backpack itself is foldable about appropriate hinge means or other foldable mechanisms so as to provide a substantially horizontal workbench area such as workbench area 20 when the present backpack is deployed in its unpacked configuration.

Figure 15:
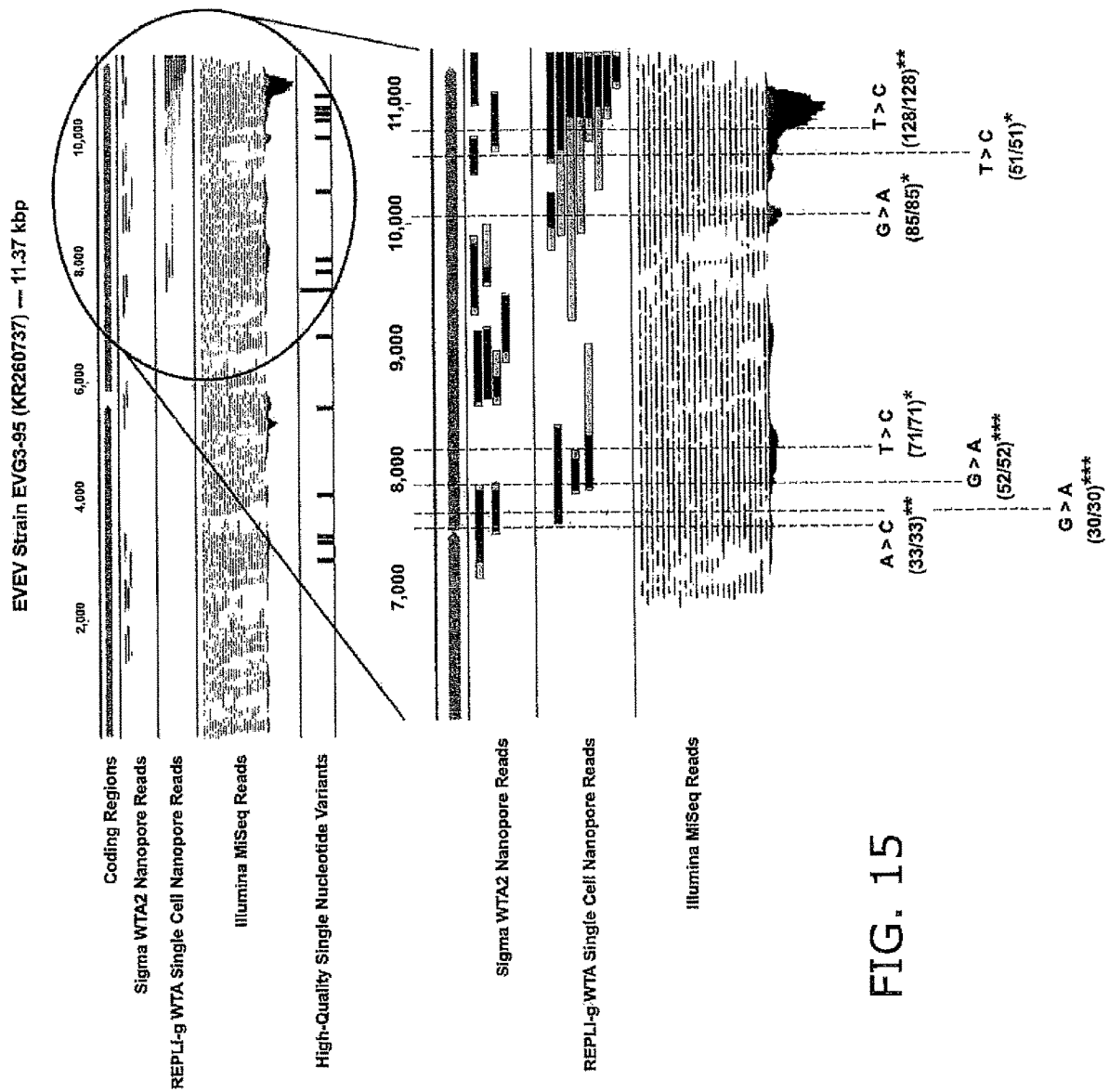
FIG. 15 is a mapping of Illumina Reads and MinION Nanopore Reads generated through Sigma WTA2 and Qiagen REPLI-g to Everglades Virus strain EVG3-95 based upon the field testing in the Florida Everglades.

A prototype of the present backpack 10 was field-tested in the Florida Everglades for mosquito surveillance. The present backpack successfully detected and sequenced pathogenic viruses directly from field samples. More particularly, gravid-traps with gravid water were used to capture Culex mosquitos. Battery powered fans drew the mosquitos into a netting where they were trapped. Typically, the physical traps such as a gravid trap for mosquitos is not housed within the present backpack 10, however other materials used for sample collection may be housed in other compartments and side pouches associated with the present backpack 10. Approximately 500 Culex Cedecei mosquitos were collected via light-baited $CO_2$ traps. Bulk RNA/DNA was extracted from sub-sampled 25 mosquito pools using the Biomeme two3 sample extraction kit. RT-qPCR was performed with an assay for VEEV, the parent species of Everglade virus (EVEV), on the Biomeme two3 device. EVEV was detected in one sample (sample 4_1) at a $C_t$ value of 33.92. Sample 4_1 was processed through the GeneReads rRNA depletion kit from QIAGEN to help reduce an abundance of host mosquito reads. The rRNA-depleted RNA was then processed through the RepliG Whole Transcriptome Amplification (WTA) for Single Cells kit. The rRNA-depleted, WTA'd cDNA, was prepped for nanopore sequencing. A total of thirty-three nanopore-generated sequence reads were found to align to the EVEV reference genomes using the sequence alignment software BWA (with nanopore-specific settings). The results of this mapping are set forth in FIG. 15. In the region where both sets of nanopore reads mapped, 7 out of 10 high-quality variants of 100% frequency detected by Illumina sequencing were also detected by nanopore sequencing. This data demonstrates strain-level arbovirus detection using the putatively included Oxford Nanopore MinION with the present invention. Only those variants detected by both Illumina and nanopore sequencing are shown. The ratio in parentheses below each variant is the ratio of Illumina reads containing the variant to Illumina read coverage at the specific location. The number of asterisks after the parentheses indicates how many nanopore reads also contained the same variant.

Figure 16:
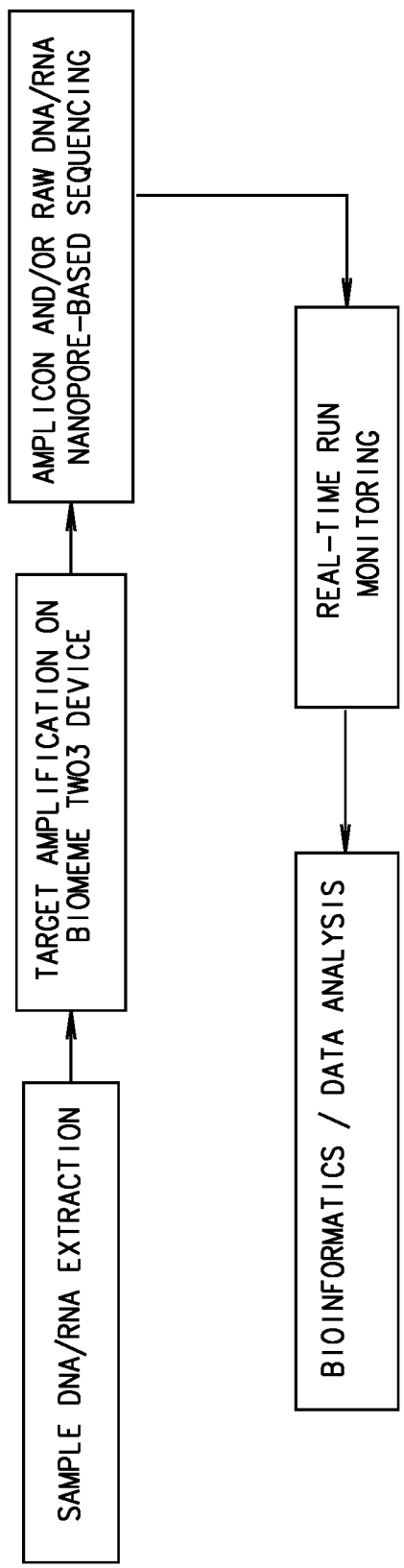
FIG. 16 is a schematic diagram of the specific protocol used in the field testing in the Florida Everglades associated with FIG. 15.

The present backpack laboratory 10 successfully extracted, amplified, sequenced and characterized viral RNA from a mosquito-pool sample. The protocol used can be run end to end with the total consumables and hardware foot print packed within the present backpack 10 or 46. Basic protocol used in the Florida Everglades test is set forth in FIG. 16. The present backpack laboratory produced sample to answer, including actionable bioinformatics reports, in less than 6 hours. This is presented as an example use-case of the present backpack laboratory and the below discussed footlocker laboratory.

FIGS. 17 and 18 illustrate still another embodiment 80 of a field-deployable mobile laboratory which can be encapsulated or otherwise configured into a footlocker configuration having the same components and capabilities as the field-deployable laboratory 10 and 46 discussed above. FIG. 17 illustrates the footlocker configuration 80 in its unpacked or deployed configuration ready for use whereas FIG. 18 illustrates the footlocker configuration 80 in its packed configuration.

As best illustrated in FIG. 17, the present footlocker laboratory 80 includes a base or box member 82 and a hinged lid member 84, both of which can be made from a wide variety of materials including a hardened heavy-duty plastic material, a wood material, a composite material, or any other suitable material for providing secure transportation and storage of all of the necessary equipment stored therewithin. The footlocker laboratory 80 includes a battery compartment 86 which can be housed in the central portion of the base member 82 as best illustrated in FIG. 17. Here again, the battery compartment 86 is configured to hold and store one or more batteries for powering all of the electrical components stored therein for at least 72 hours of continuous use as previously described. The battery compartment 86 can include one or more Li-ION batteries to provide the required power. In addition, the base member 82 likewise includes a plurality of storage compartments such as compartments 88, 90, 92 and 94 which are housed therewithin, each compartment 88-94 being configured in the form of slide-out drawers which can be extended as illustrated in FIG. 17 when the present footlocker laboratory 80 is deployed for use. In this regard, the slide-out drawers or compartments 88-94 can be configured for selective movement into and out of the base member 82 through the use of conventional brackets and other conventional mechanisms for allowing the compartments or drawers 88-94 to be moved between a stored or closed position totally within the footprint of the base member 82 when the laboratory 80 is in its packed condition as illustrated in FIG. 18 and a deployed or open position wherein the compartments can be extended at least partially outside of the footprint of the base member as illustrated in FIG. 17 so as to have access to the components stored within each such compartment. In the embodiment illustrated in FIG. 17, one end portion of each of the compartments 88-94 can abut the central compartment 86 when the compartments 88-94 are in their stored position.

More particularly, compartment 88 is configured and specifically designed for housing the cooling/freezer components of the present system such as the phase-change cooling system 22 previously described. The cooling compartment 88 can be a single compartment or it can be segregated into two or more compartments depending upon the particular application. As previously described, one compartment can hold critical lab reagents at 4° C., and, if necessary, another compartment can hold lab reagents at −20° C. These compartments can be used to hold and store priority samples after collection requiring cold storage as previously explained. Here again, maintaining the required temperatures within compartment 88 is accomplished through the use of phase-change proprietary liquid mixtures as previously described with respect to FIG. 3.

Still further, compartment 90 can be configured to store all of the necessary ancillary equipment including pipettes, reagent bottles, tube racks and other consumables as previously explained with respect to mobile laboratories 10 and 46. Compartment 92 is configured to house the PCR system such as the Biomeme system previously described, and compartment 94 is configured to house a mini centrifuge and vortex as previously explained. Importantly, a substantially horizontal workbench member 96 overlays all of the compartments 86-94 and provides a substantially flat workspace for positioning a computer monitor, keyboard, and other data analysis equipment as necessary. The workbench member 96 can be configured so as to be removable from the upper portion of the base member 82 so as to likewise provide access to the battery compartment 86 as well as the other compartments 88-94. The workbench area can be an acid-resistant Plexiglass member or other suitable acid-resistant material for easy sterilization after use.

The footlocker lid member 84 is hingedly attached to the base member 82 as illustrated in FIG. 17 and includes a plurality of pockets or compartments such as compartments 98, 100, 102 and 104 for again storing and housing required components for accomplishing the detection, amplification, sequencing and analysis of various specific viruses, pathogens, bacteria and other infectious diseases accumulated in the field. These compartments are housed within the lid member 84 as best illustrated in FIG. 17. The lid member 84 is pivotally movable between a first position wherein the lid member overlays the box member 82 and closes access to the box member, and a second or open position wherein the lid member is removed from the box member 82 and allows access to the box member.

More particularly, compartment 98 can be specifically designed and configured to house the CPU unit associated with the present mobile laboratory. This compartment also includes the bioinformatics analysis system such as the Intel NUC system as previously explained which provides the computing platform for the bioinformatics analysis of sequencing data. This compartment also houses the motherboard and other electronics associated with the CPU unit. All of these components can be inserted into compartment 98 and can be easily accessed and can be pulled or otherwise slid out of compartment 98 for access.

Compartment 100 is specifically configured and designed for holding a pop-up monitor, keyboard, track pad for data analysis and other associated equipment. These components again can be easily slid into and slid out of compartment 100 for both storage and use in the field. In similar fashion, compartment 102 is specifically designed and configured to hold a cellular wireless connecting module such as a 4G/LTE module which again can be slid into and out of compartment 102 for access. Compartment 104 is specifically designed and configured to hold the DNA sequencing system such as the MinION nanopore sequencer as previously described. Still further, the footlocker lid member 84 likewise includes a plurality of power outlets such as outlets 106, 108, 110 and 112 illustrated in FIG. 17 for powering still additional equipment needed for the detection, sequencing and analysis of the targeted agents and toxins. These power outlets can be USB3 and/or standard Nema 5-15 type B power outlets.

The CPU unit, the cellular wireless connecting module, the DNA/RNA sequencing and the monitor, keyboard and trackpad are all selectively movable between a first position wherein such components are within their respective compartments 98, 100, 102 and 104 and a second position wherein such components are at least partially outside of their respective compartments for access.

Importantly lid member 84 includes at least a pair of extendable, telescoping leg members 114 and 116 as best illustrated in FIGS. 17 and 18 for supporting the lid member 82 in a substantially flat horizontal position in substantial alignment with the workbench member 96 of base member 82. In similar fashion, lid member 84 includes a substantially flat horizontal workbase member 118 which overlays the compartments 98-104 and power outlets 106-112 so as to again provide a substantially flat surface for supporting equipment thereon. When lid member 84 is pivotally rotated to its open position, leg members 114 and 116 can be extended or telescopingly positioned so as to support lid member 84 in a position wherein the workbench member 118 is in substantial alignment with workbench area 96 of base member 82. This provides a uniform extended workbench area for supporting the monitor, keyboard, track pad for data analysis and other associated equipment necessary for detection, genomic characterization and bioinformatics analysis and reporting in the field.

FIG. 18 illustrates the present footlocker mobile laboratory 80 in its closed or packed configuration. In this regard, the extendable leg members 114 and 116 can be pivotally mounted to the top portion of lid member 84 through the use of conventional pivot mechanisms 120 and 122 such that when the lid member 84 is pivotally rotated to its open position, leg members 114 and 116 can likewise be pivotally rotated to a substantially vertical position as illustrated in FIG. 17 so as to support lid member 84 in its deployed configuration. Lid member 84 likewise includes a securing clip, strap or bracket member such as members 124 and 126 for holding the leg members 114 and 116 in a stored condition on top of lid member 84 when the mobile laboratory 80 is in its packed configuration. The adjustability of the leg members can be accomplished using known methods. Leg members 114 and 116 fold into a small configuration when the footlocker laboratory 80 is in its packed condition as illustrated in FIG. 18. It is also recognized and anticipated that other leg member configurations and folding and extendable mechanisms can be utilized in order to support the lid member 84 in its deployed and operational position as discussed above. Locating the leg members 114 and 116 at other locations associated with lid member 84 are also anticipated and envisioned.

The present footlocker configuration 80 can be easily deployable on the tail-gate of a pick-up truck or a fold-out table in the field. The present system 80 closes up into a rugged, drop-resistant, secure box configuration and it unfolds into a comprehensive molecular biology workstation. It is also recognized and anticipated that the computing and analysis components associated with the present system 80 such as the PCR system, the DNA sequencing system, appropriate electrical connections between the battery array 86 and the other components of the present system needing electrical power such as the CPU unit, the 4G/LTE module, the power outlets, the centrifuge and the Biomeme system can be accomplished through a conventional power connection means such as through conductive paths 128 illustrated in FIG. 17. It is also recognized and anticipated that all of the various components discussed above can be housed in different compartments and that the various compartments can be moved and repositioned to other locations within the base member 82 and the lid member 84. Other configurations of the footlocker mobile laboratory 80 are likewise envisioned and anticipated and it is preferred that the footlocker laboratory 80 be deployable in its unpacked configuration so as to provide a substantially horizontal workbench area or surface such as the workbench areas 96 and 118 for operational use in the field. Other configurations of the footlocker laboratory 80 are likewise anticipated and envisioned for future use.

FIGS. 19-28 illustrate still another embodiment 130 of a field-deployable mobile laboratory which can be encapsulated or otherwise configured into a footlocker type configuration having many of the same components and capabilities as the field-deployable laboratories 10, 46 and 80 discussed above. FIG. 19 illustrates the footlocker configuration 130 in its closed and packed configuration whereas FIGS. 20-23 and 25 illustrate the footlocker configuration 130 in its unpacked or deployed configuration ready for use. Like field-deployable laboratories 10, 46 and 80, field-deployable laboratory 130 can be configured for supporting devices for a wide variety of different applications including, but not limited to, point of care diagnostics, mobile DNA extraction, amplification and sequencing, field forensics, environmental monitoring, disease surveillance, sequence-based human identification using DNA traces, computational analysis and much more. The present portable laboratory 130 addresses the logistical challenges inherent to using fieldable sequencing devices and forward-operating environments. It is a compact, agile laboratory integrating equipment and hardware for a wide variety of different applications including an integrated battery supply capable of powering the workstation and cold chain cooling compartments for holding, maintaining and storing critical cold reagents and samples at 4° C. and −20° C. as previously explained above with respect to field-deployable laboratories 10 and 46, if cold-chain solutions are required for a particular application. The mobile laboratory 130 opens into a workstation having a workbench array which includes consumables and hardware strategically configured for intuitive accessibility during common workflow patterns as will be hereinafter further explained. The integrated computational workstation harbors all required equipment and software to operate a PCR system and a MinION nanopore sequencer as previously explained above. The laboratory 130 closes into a single, lockable, stackable unit as illustrated in FIG. 19 and it is also weatherproof.

As best illustrated in FIGS. 19-21, the present footlocker laboratory 130 includes a first footlocker member 132 and a second footlocker member 134 which are hinged together using conventional means as best illustrated in FIGS. 20 and 21. Footlocker member 134 is movable between a first position wherein member 134 overlaps footlocker member 132 as illustrated in FIG. 19 so as to close access to member 132 and a second position wherein member 134 provides access to member 132 as illustrated in FIGS. 20 and 21. Footlocker members 132 and 134 can be made from a wide variety of materials including a hardened heavy-duty plastic material, a composite material, or any other suitable material for providing secure transportation and storage of all of the necessary equipment stored therewithin. The members 132 and 134 are likewise preferably weatherproof and are latched or otherwise locked together in their closed position using conventional cooperatively engageable locking means such as locking means 135.

In the embodiment illustrated in FIGS. 20-23, the first member 132 includes a cavity 136 for housing a phase-change cooling system such as cooling system 22 discussed above. Cooling compartments 138 and 140 are segregated as previously explained, compartment 138 holding critical lab reagents at 4° C. and compartment 140 holding lab reagents at −20° C. The compartments can also hold and store priority samples after collection. Maintaining reagents and samples at 4° C. and/or −20° C. for up to 72 hours is accomplished by phase change proprietary liquid mixtures as previously explained.

Figure 23:
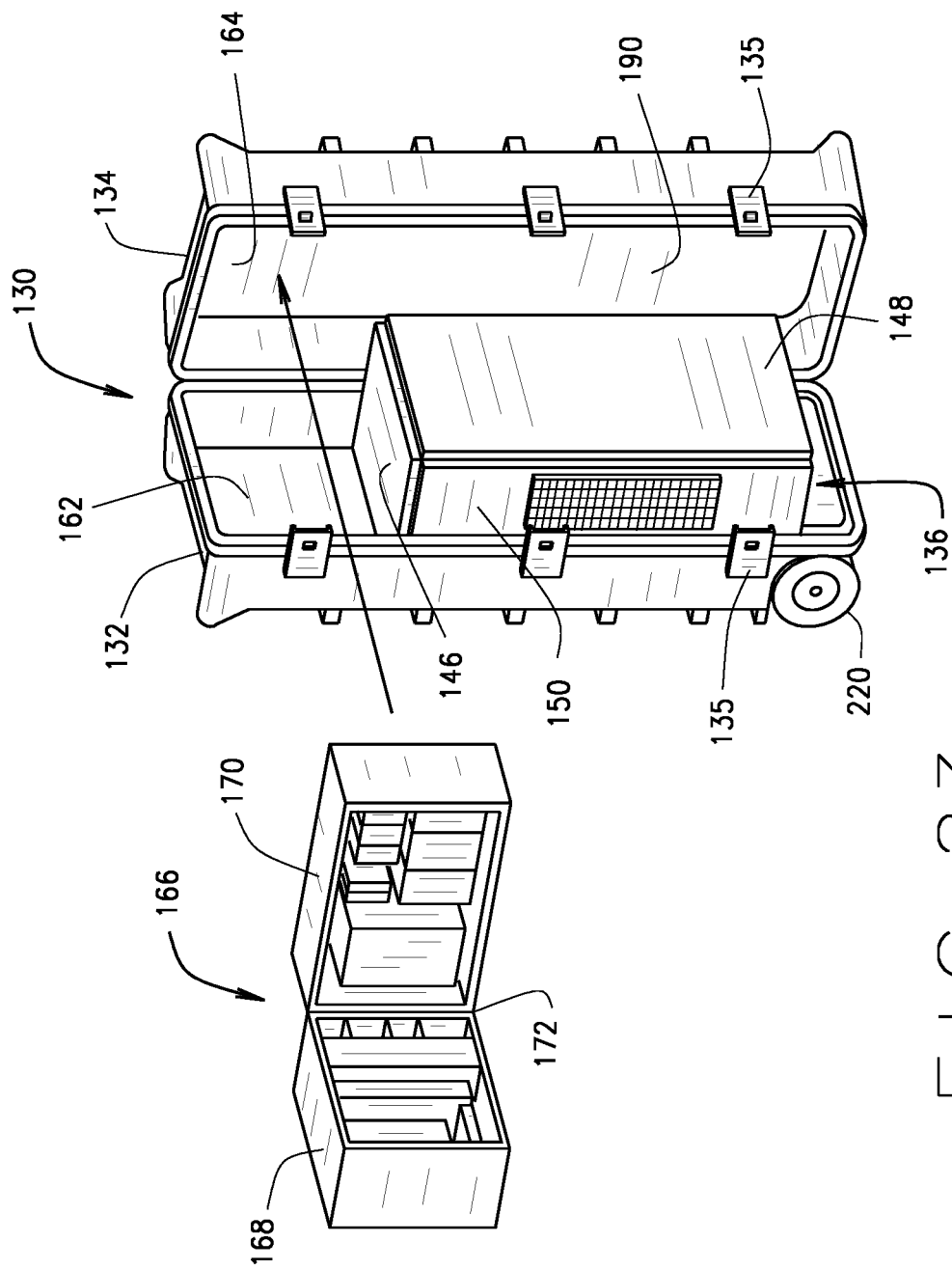

For those field applications where cold storage of reagents and samples is not necessary, compartments 138 and 140 can be used to house other necessary laboratory equipment infrastructure for on-site molecular biosurveillance including, but not limited to, PCR-detection, genomic sequencing, and bioinformatics analysis. This equipment as well as other equipment can be housed in compartments 138 and 140 associated with first member 132 as best illustrated in FIGS. 21-23. Compartments 138 and 140 can include the necessary PCR system, a DNA/RNA sequencing system and a mobile bioinformatics analysis system as previously explained with respect to mobile laboratories 10, 46 and 80. For example, the mobile bioinformatics analysis system can include a CPU unit such as the Intel NUC device; the PCR system can include the Biomeme Two3q PCR system; and a DNA sequencing system can include the Oxford Nanopore Minion Mk1 system as explained above. It is also recognized and anticipated that other CPU units, PCR systems and other comparable DNA/RNA sequencing systems can likewise be utilized depending upon the particular application. These systems provide the necessary hardware and computational systems for detecting, sequencing and analyzing particular biological targets as explained above.

Like mobile laboratories 10, 46 and 80, mobile laboratory 130 likewise includes a battery compartment 142 which is configured to hold and store one or more batteries for powering all of the electrical components stored within laboratory 130 for any appropriate time period depending upon the particular application including up to at least 72 hours of continuous use as previously described. Battery compartment 142 can include one or more Li-Ion batteries to provide the required power. It is recognized and anticipated that any suitable battery or battery array can be utilized as the power supply and can provide the required power necessary depending upon the particular field application that the present unit 130 is specifically designed for.

Mobile laboratory 130 likewise includes a foldable bench-top workspace member 144 as best illustrated in FIGS. 20 and 21, the workbench table top member 144 including a first table top portion 146 which is positioned and located at least partially within the cavity 136 and is fixedly attached to the first member 132 above compartment 140 as best illustrated in FIGS. 20 and 21 and a second table top portion 148 which is hingedly attached to the first table top portion 146 as illustrated. The first table top portion 146 divides cavity 136 into two separate cavities or spaces 162 and 165 and the second table top portion 148 folds downwardly over the top of compartments 138, 140 and 142 as illustrated in FIG. 20. The second table top portion 148 is movable between a first position wherein the workbench 144 extends perpendicular to the cavity 136 and a second position wherein table top portion 148 overlap compartments 138, 140 and 142 adjacent to cavity 165. In addition, the second table top portion 148 of workbench 144 includes a third keyboard table top portion 150 which is hingedly attached to table top portion 148 as illustrated in FIG. 21 and is foldable adjacent the side portion of compartments 138, 140 and 142 as best illustrated in FIG. 20. In this particular embodiment, the workbench 144 folds over the top and partially encases compartments 138, 140 and 142 as previously explained so as to be compatible for storage when the mobile laboratory 130 is in its closed position as illustrated in FIG. 19 and as will be hereinafter further explained.

Workbench 144 may likewise include a pair of extendable and adjustable leg members 152 as best seen in FIGS. 21 and 22. Extendable leg members 152 can be pivotally mounted to the underside portion of the terminal end portion of table top portion 148 through the use of conventional pivot mechanisms (not shown) such that when table top portion 148 is moved to its extended position as shown in FIG. 21, leg members 152 can likewise be pivotally rotated to a substantially vertical position so as to support table top portion 148 in its deployed substantially horizontal position. The adjustability of the leg members 152 can be accomplished using known methods and leg members 152 can be adjusted to account for uneven terrain at the point of setup.

Leg members 152 can also fold up underneath workbench portion 148 so as to lie adjacent the underside portion of table top 148 when workbench 144 is folded into its packed condition as illustrated in FIG. 20. In this regard, the leg members 152 can lie adjacent the top portion of compartments 138, 140 and 142, or leg members 152 can straddle compartments 138, 140 and 142 and lie adjacent their respective side portions. It is also recognized and anticipated that other leg member configurations and folding and extendable mechanisms can likewise be utilized in order to support workbench 144 in its deployed and operational position as discussed above and as will be discussed with respect to FIG. 25. Locating leg members 152 at other locations associated with workbench 144 are also anticipated and envisioned.

The leg members 152 can be held in their stored position adjacent the underside portion of table top portion 148 through the use of conventional C-clamps or straps associated with the underside portion of benchtop portion 148. Other methods and devices for holding the leg members in their stored position are likewise anticipated and envisioned.

FIG. 22 illustrates another embodiment of workbench 144 wherein foldable keyboard table top portion 150 is now replaced with a hinged table top portion 154 which includes a first portion 156 and a second portion 158. Hinged keyboard table top portion 154 is designed for holding a keyboard associated with a computer as illustrated in FIG. 22 and is foldable at hinge portion 160 so as to lie adjacent to and flush with hinged portion 156 so that keyboard table top portion 154 can likewise be stored adjacent the side portions of compartments 138, 140 and 142 as illustrated in FIG. 20. Table top portion 158 allows the keyboard to be positioned at a lower vertical position as compared to the main workbench table top 148 for ergonomic purposes.

As best illustrated in FIG. 22, the space 162 located in the first footlocker member 132 located above the fixed workbench member 146 is compatible for being configured into one or more compartments for holding a wide variety of other various components and materials necessary for field testing samples taken in the field depending upon the particular application of the field-deployable laboratory 130 such as pouches, pipettes, pipette tip boxes, sample tubes and tube racks, the storage location for a mini centrifuge, reagent bottles, and other consumables and associated equipment necessary for accomplishing the task at hand including, but not limited to, the detection genomic characterization and bioinformatics analysis and reporting in the field. The space 162 may include a plurality of pockets or compartments as illustrated in FIG. 22 and the corresponding space 164 located in the second footlocker member 134 above workbench 144 can likewise be similarly configured as best shown in FIG. 22 for again storing and housing required components for accomplishing the detection, amplification, sequencing and analysis of various specific viruses, pathogens, bacteria and other diseases accumulated in the field, or for other desired purposes including equipment and technology for human identification using DNA traces.

In addition, the spaces or cavities 162 and 164 can likewise be structured and configured so as to hold a small mobile backpack member such as backpack member 166 as best illustrated in exploded FIG. 23. In this particular embodiment, backpack member 166 includes backpack portions 168 and 170 which are hinged in a conventional manner at hinge point 172 so as to be configured in a closed state as illustrated in FIG. 20 and in an open state as illustrated in FIG. 23. Backpack portion 168 is designed to fit into the interior space 162 of first footlocker member 132 and backpack portion 170 is configured to fit within the interior space 164 of footlocker member 134 when in its open position as illustrated in FIG. 23. When in its closed position as illustrated in FIG. 20, backpack member 166 has an overall profile no greater than compartments 138, 140 and 142 as illustrated. In this regard, the second footlocker member 134 likewise includes a lower internal space or cavity 190 as best illustrated in FIGS. 20 and 23 which is configured to at least partially receive compartments 138, 140 and 142 as well as workbench 144 when positioned in its collapsed and stored position as shown in FIGS. 20 and 23 when the second footlocker member 134 is moved to its closed position as illustrated in FIG. 19. In this embodiment, backpack member 166 can likewise hold a lot of the same ancillary equipment including pipettes, reagent bottles, tube racks and other consumables necessary for a particular application as previously explained with respect to mobile laboratories 10, 46 and 80 including a PCR system and a DNA/RNA sequencing system.

Figure 24:
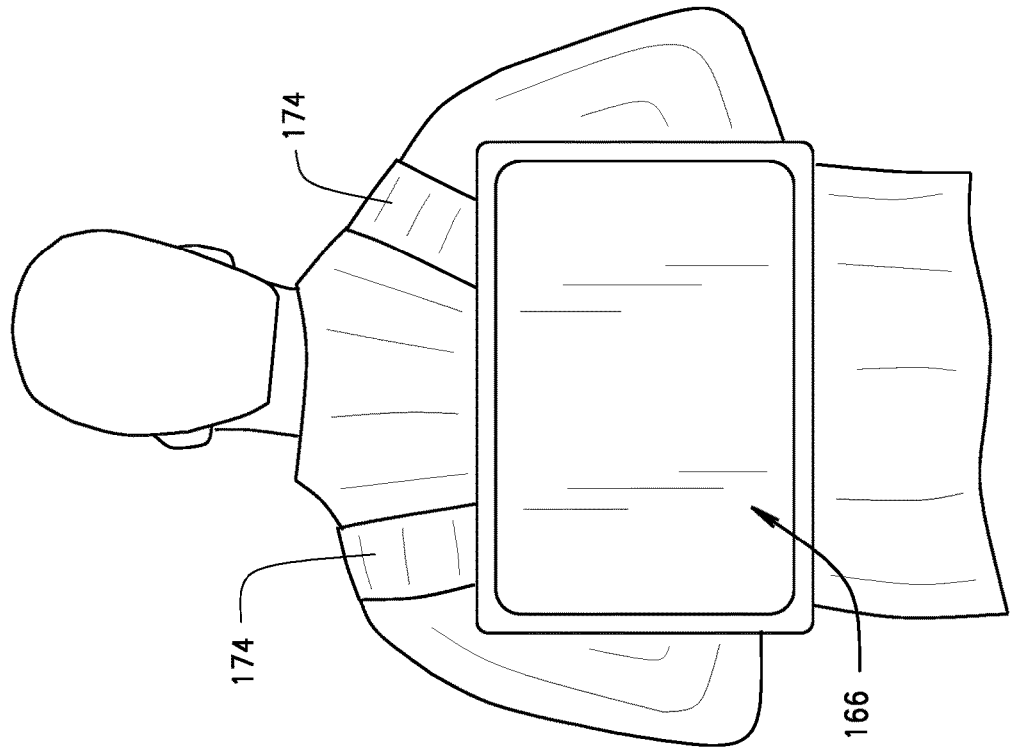

As best illustrated in FIG. 24, removable backpack member 160 can be removed from the mobile footlocker laboratory 130 and can be taken by a user into the field away from where mobile laboratory 130 has been established as shown in FIGS. 21 and 22 for further penetration into the field for collecting and gathering field samples. In this regard, backpack member 166 can include a pair of adjustable backstrap members 174 (FIG. 24) for allowing a user to easily carry backpack member 166 as illustrated. The backpack member 166 can be configured to carry any necessary equipment for targeting specific pathogens and other biological selected agents and toxins depending upon the particular application.

The mobile backpack member 166 can be held in the respective internal spaces 162 and 164 when in its closed and open positions using any suitable means such as hook and loop fasteners associated with both back portions of members 168 and 170 and the internal spaces 162 and 164, and through webbing, straps and/or side release clips associated with members 168 and 170 as well as internal spaces 162 and 164. Other conventional means for holding the backpack member 166 within the corresponding spaces 162 and 164, both in its open and closed positions, are also anticipated and envisioned.

Figure 25:
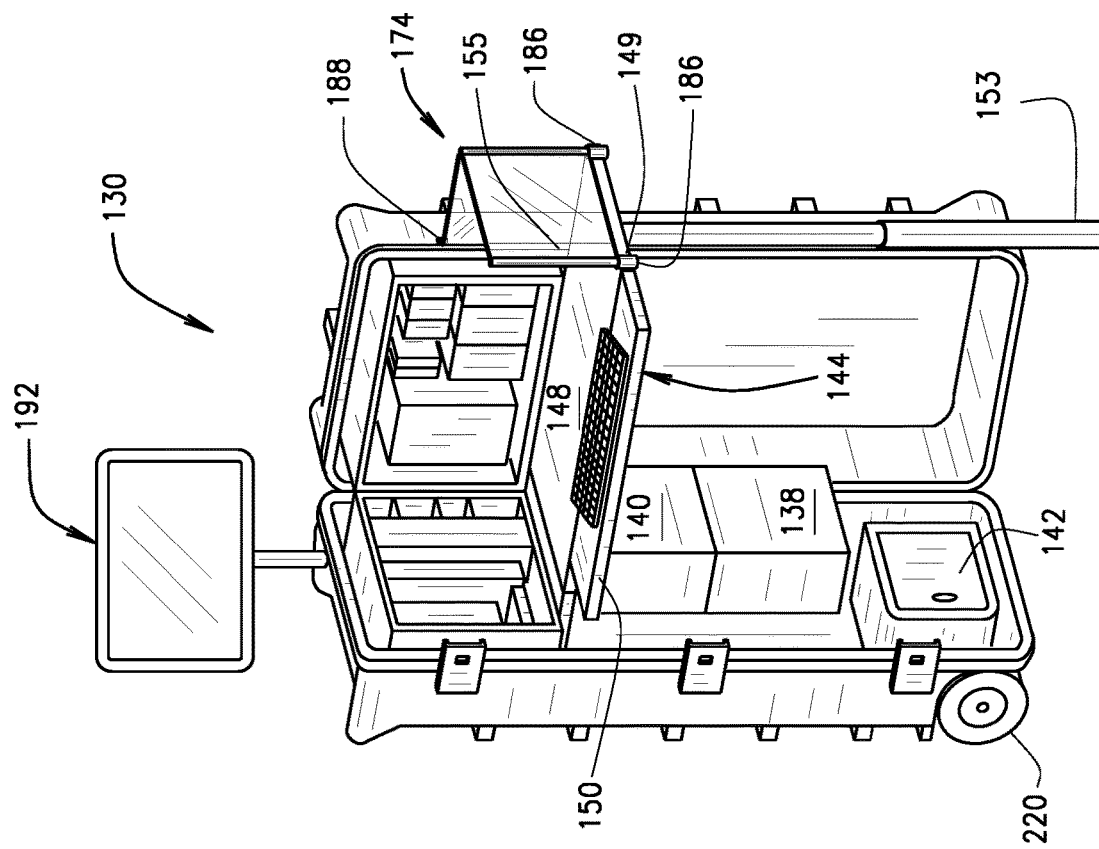

FIG. 25 illustrates still another embodiment of the workbench structure 144 wherein the workbench member 148 is held in a substantially horizontal position through the use of a single extendable leg member 153, similar to leg members 152, wherein leg member 153 is pivotally or otherwise attached to the front corner 149 of workbench member 148 as illustrated in FIG. 25. In addition, leg member 153 may be held in operative position through the use of a locking leg adaptor mechanism (not shown) attached to the underside portion of front corner 149 wherein leg member 153 can be separately attached to the leg adapter for use and thereafter removed for storage within the members 132 and/or 134. In this particular embodiment, workbench table top member 148 can be further secured to the second footlocker member 134 at attachment point 155. The attachment mechanism at 155 can include any suitable means for supporting workbench member 148 at attachment point 155 such as any bracket arrangement attachable to or otherwise associated with the second footlocker member 134. Use of the single leg member 153 in conjunction with the attachment mechanism at attachment point 155 can provide sufficient structure and stability to the workbench table top members 148 and 150 thereby reducing the weight of the overall portable laboratory 130.

The workbench structure 144 can likewise include a windshield member 174 as best illustrated in FIGS. 21 and 25. Windshield member 174 includes a first panel member 176 and a second panel member 178 which are positioned adjacent an open end portion of workbench 144 as best illustrated in FIGS. 21, 22 and 25 so as to shield the workbench surface and the user from wind and other blowing debris if necessary. The windshield members 176 and 178 can be hingedly attached to each other at corner portion 180 and include attachment members 182 and 184 as best illustrated in FIGS. 21, 22 and 25 which are engageable with a pair of engaging sockets 186 located at the terminal end portion of workbench member 148 as best illustrated in FIGS. 21, 22 and 25. The opposite end portion of windshield member 174 adjacent the second footlocker member 134 is removably attachable to the second footlocker member 134 via attachments points 188 as best illustrated in FIG. 22. Attachment points 188 can be any type of clamping mechanism or other fastening means for holding the one end portion of windshield member 174 adjacent the edge portion of the second footlocker member 134 as illustrated in FIGS. 21 and 25. Windshield panel members 176 and 178 can likewise be two separate rigid panels each attachable to the terminal end portion of workbench member 148 as previously explained. In this regard, at least one engaging socket 186 can receive two attachment members 182 or 184, or an additional engaging socket 186 can be added to the terminal end portion of workbench member 148. Other mechanisms for attaching the windshield member 174 to the workbench 144 are likewise anticipated and envisioned. Windshield member 174 can be stored within the field-deployable footlocker laboratory 130 adjacent workbench portion 150 in its stored position as best illustrated in FIG. 20 or it can be conveniently stored, attached or otherwise held either within the lower cavity 190 of the second footlocker member 134 or under workbench table top member 148 via straps, Velcro attachment means, or other suitable holding mechanisms.

Figure 26:
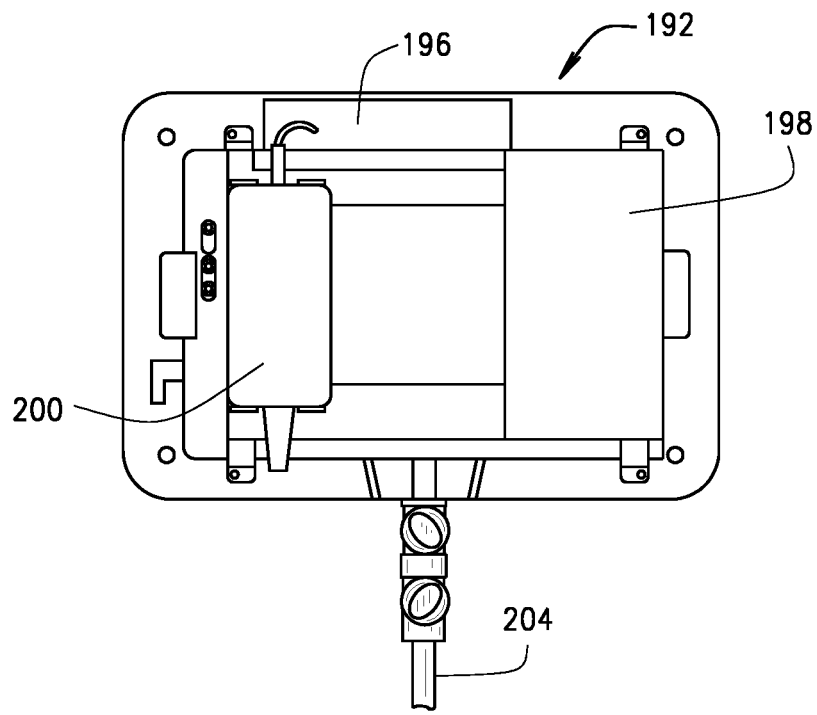
Figure 27:
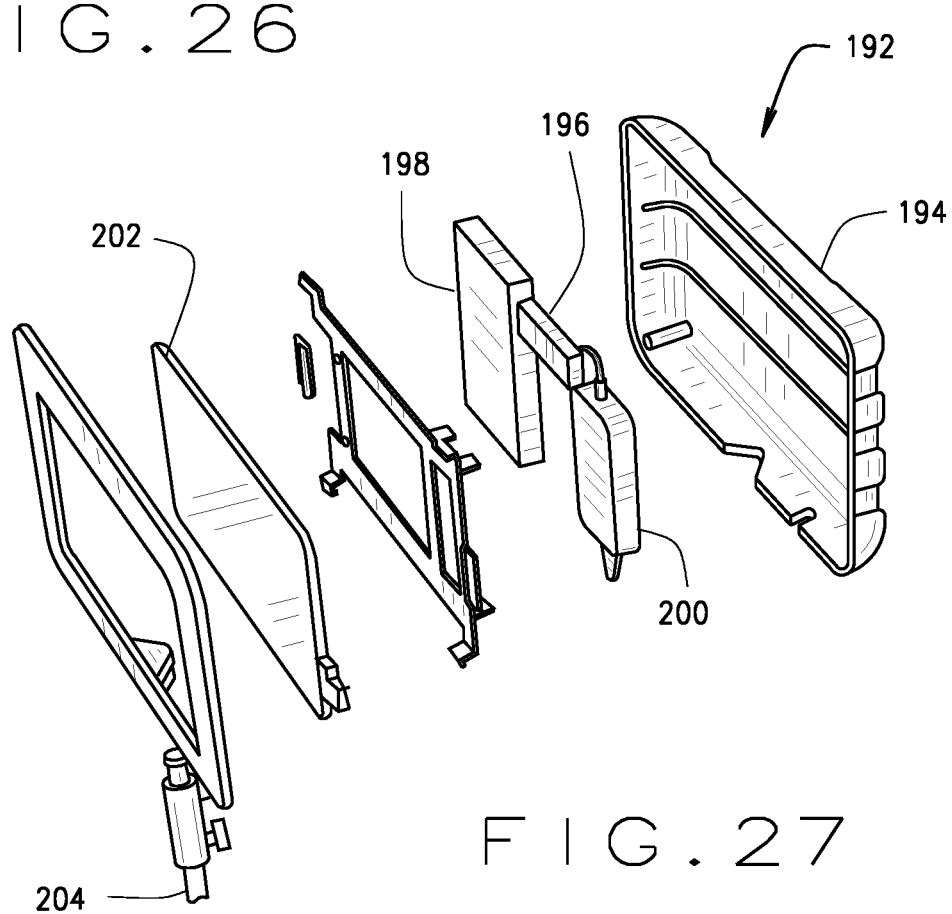

Like field-deployable laboratories 10, 46 and 80, in the embodiment of mobile laboratory 130 where the cold storage compartments 138 and 140 are utilized, all of the necessary components for a solid state computing system for local analytical needs including the Intel NUC system (CPU unit), a 4G/LTE modem, and other ancillary equipment can all be housed within the computer monitor structure 192 as best illustrated in FIGS. 26 and 27. As best illustrated in FIG. 27, the computer monitor structure 192 includes a rear cover member 194 which houses the modem 196, the NUC system 198 and the NUC power supply (NUC PS) 200, a typical monitor display 202 such as the HP EliteDisplay S140u unit as well as the necessary frame work to hold the same. The computer monitor structure 192 includes an attachment member 204 which is received into a corresponding socket or receptacle 206 associated with the top edge portion of the first footlocker member 132 as best illustrated FIGS. 21, 22, 25 and 28. The receptacle 206 can be located anywhere along the top edge portion of the first footlocker member 132 such as towards the rear or hinged portion of members 132 and 134 as illustrated in FIGS. 21, 22, 25 and 28 or towards the front edge portion of member 132. It is recognized and anticipated that the receptacle 206 can be located anywhere along the top edge portion of member 132. In addition, any suitable cooperating means for holding and attaching attachment member 204 within the receptacle 206 is likewise recognized and anticipated.

Figure 28:
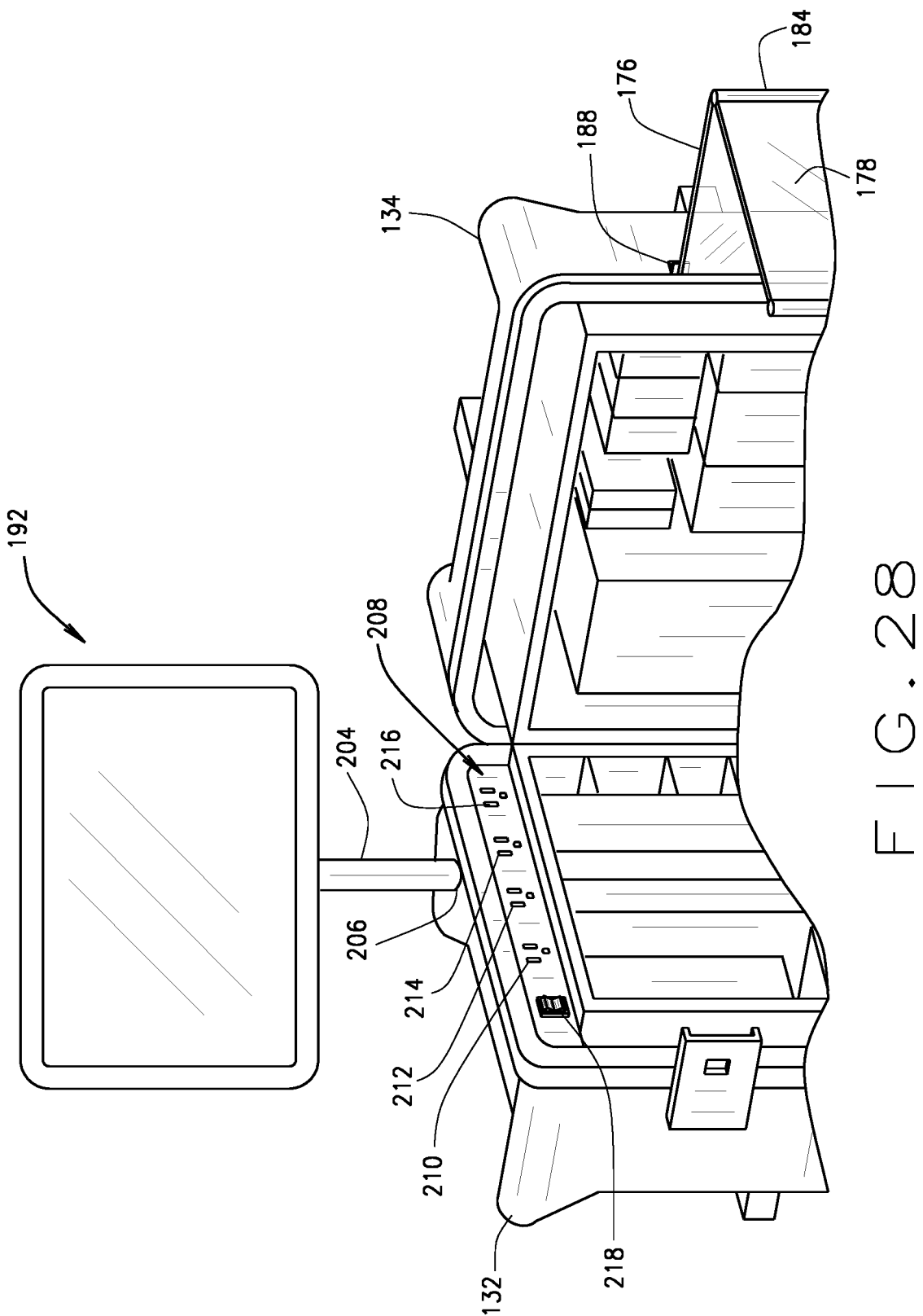

All of the electrical components associated with computer monitor structure 192 can be plugged into power strip 208 associated with the top portion of the first footlocker member 132 as best illustrated in FIG. 28. Power strip 208 can include a plurality of power outlets such as outlets 210, 212, 214 and 216 as illustrated in FIG. 28 for powering not only the electronics associated with computer monitor 192, but still other additional equipment needed for the detection, sequencing and analysis of the targeted agents and toxins. The battery array housed in compartment 142 is hard wired to the power strip 208 and includes an on off switch 218 as illustrated. All of the electronic equipment associated with the present footlocker laboratory 130 including the Intel NUC system, the Oxford Nanopore MinIon sequencer, the PCR system and other computing systems which have been described above with respect to portable laboratories 10, 46 and 80 can also be plugged into power strip 208 if necessary.

The computer monitor structure 192 can be housed in the upper cavity 164 associated with the second footlocker member 134 and it can be held in place via conventional straps and/or Velcro attachment means. The computer monitor structure 192 abuts the mobile backpack unit 166 when the laboratory 130 is in its closed stored condition and must be removed from cavity 164 before the mobile backpack unit 166 is opened as illustrated in FIG. 21. Removing the computer monitor structure 192 from cavity 164 provides sufficient space for the mobile backpack portion 170 to open fully into the cavity space 164. Here again, it is recognized and anticipated that the computer monitor structure 192 may likewise be housed in other locations associated with the present footlocker laboratory 130 such as in the lower cavity 165 associated with the second footlock member.

The present footlocker configuration 130 likewise includes a pair of wheels 220 and a handle member 222 for easy maneuverability of the entire unit by a single person. The unit 130 can be easily deployable on the tailgate of a pickup truck and it closes up into a rugged, drop resistant, secure box configuration. In addition, the footlocker structure 130 can likewise be made so as to be stackable and nestable with each other. In other words, the top portion of the second footlocker member 134 can include a plurality of ridges and grooves which are cooperatively engageable with a corresponding set of ridges and grooves associated with the bottom portion of the first footlocker member 130. This stackability and nestability is important if multiple units are being transported as this configuration saves space in the transportation vehicle. It is also recognized and anticipated that all of the various components discussed above with respect to footlocker unit 130 can likewise be housed in different compartments and that various compartments can be moved and repositioned to other locations within the first and second footlocker members 132 and 134. Other configurations of the footlocker mobile laboratory 130 are likewise envisioned and anticipated and it is preferred that the footlocker laboratory 130 be deployed so as to provide a substantially horizontal workbench area or surface such as workbench areas 144 and 150 for operational use in the field. Other configurations of the footlocker laboratory 130 are likewise anticipated and envisioned for future use.

The various constructions and configurations of the present mobile backpack laboratories 10 and 46 and the present mobile footlocker laboratories 80 and 130 described above and illustrated in the various drawings are represented by way of example only and are not intended to limit the concepts and principles of the present invention. Thus, there has been shown and described several embodiments of a novel modular, mobile field-deployable laboratory for the detection, sequencing and analysis of targeted viruses, pathogens, bacteria and other emerging infectious diseases. As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present constructions will, however, become apparent to those skilled in the art after considering the specification and the accompanying drawings. All such changes, modifications, variations and other uses and applications which do not depart from the spirit and scope of the invention are deemed to be covered by the invention and is limited only by the above-described specification and accompanying drawings.

What is claimed is:

1. A mobile field-deployable laboratory for detecting and analyzing biological targets comprising:
    a first member having a cavity formed therewithin;
    a workbench member having at least a portion thereof positioned and located within the cavity of said first member so as to divide the cavity of said first member into a first cavity portion and a second cavity portion, at least a portion of said workbench member being movable between a first position wherein said workbench member extends perpendicular to said first and second cavity portions and a second position wherein at least a portion of said workbench member lies adjacent to one of said first and second cavity portions;
    a second member hingedly attached to said first member, said second member being movable between a first position wherein said second member overlays the first member and closes access to said first member and a second position wherein said second member provides access to said first member, said second member having at least one cavity formed therewithin, said at least one cavity associated with said second member at least partially receiving said workbench member when said workbench member is in its second position and said second member is in its first position;
    at least one leg member for supporting the workbench member in a position perpendicular to said first and second cavity portions of said first member; and
    a mobile backpack unit associated with one of said first and second cavity portions of said first member, said mobile backpack unit being configured for housing ancillary equipment and being at least partially received by the at least one cavity of said second member when said second member is in its first position.

2. The mobile field-deployable laboratory of claim 1 including at least one compartment associated with said first member configured to house a cooling system.

3. The mobile field-deployable laboratory of claim 2 wherein the cooling system includes a phase-change cooling system capable of holding a predetermined selected temperature constant for a predetermined time period.

4. The mobile field-deployable laboratory of claim 1 wherein the mobile backpack unit includes a first backpack member and a second backpack member, the first backpack member being receivable within one of said first and second cavity portions of said first member and the second backpack member being receivable within the at least one cavity of said second member when said second member is in its second position.

5. The mobile field-deployable laboratory of claim 1 further including a computer system for analyzing biological target agents.

6. The mobile field-deployable laboratory of claim 5 wherein said computer system includes a monitor structure attachable to said first member.

7. The mobile field-deployable laboratory of claim 6 wherein the computer system includes at least one computer system component, which computer system component being housed within the monitor structure.

8. The mobile field-deployable laboratory of claim 7 wherein the monitor structure includes a computer display screen, a modem, a Next Unit of Computing "NUC" system, and the power supply for the NUC system.

9. The mobile field-deployable laboratory of claim 1 wherein the mobile backpack unit houses a Polymerase Chain Reaction ("PCR") system.

10. The mobile field-deployable laboratory of claim 1 wherein the mobile backpack unit houses a DNA sequencing system.

11. A mobile field-deployable laboratory for detecting and analyzing biological targets comprising:
    a first member having a cavity formed therewithin;
    a workbench member having at least a portion thereof positioned and located within the cavity of said first member so as to divide the cavity of said first member into a first cavity portion and a second cavity portion, at least a portion of said workbench member being movable between a first position wherein said workbench member extends perpendicular to said first and second cavity portions and a second position wherein at least a portion of said workbench member lies adjacent to one of said first and second cavity portions;
    a second member hingedly attached to said first member, said second member being movable between a first position wherein said second member overlays the first member and closes access to said first member and a second position wherein said second member provides access to said first member, said second member having at least one cavity formed therewithin, said at least one cavity associated with said second member at least partially receiving said workbench member when said workbench member is in its second position and said second member is in its first position;
    at least one leg member for supporting the workbench member in a position perpendicular to said first and second cavity portions of said first member; and
    a windshield member attachable to at least a portion of said workbench member.

12. A mobile field-deployable laboratory for detecting and analyzing biological targets comprising:
    a first member having a cavity formed therewithin;
    a workbench member having at least a portion thereof positioned and located within the cavity of said first member so as to divide the cavity of said first member into a first cavity portion and a second cavity portion, at least a portion of said workbench member being movable between a first position wherein said workbench member extends perpendicular to said first and second cavity portions and a second position wherein at least a portion of said workbench member lies adjacent to one of said first and second cavity portions;
    a second member hingedly attached to said first member, said second member being movable between a first position wherein said second member overlays the first member and closes access to said first member and a second position wherein said second member provides access to said first member, said second member having at least one cavity formed therewithin, said at least one cavity associated with said second member at least partially receiving said workbench member when said workbench member is in its second position and said second member is in its first position; and at least one leg member for supporting the workbench member in a position perpendicular to said first and second cavity portions of said first member;

wherein said at least one leg member includes a pair of adjustable members for supporting the workbench member in a position perpendicular to said first and second cavity portions of said first member.

13. The mobile field-deployable laboratory of claim 12 wherein said pair of leg members are pivotally connected to said workbench member.

14. A mobile field-deployable laboratory for detecting and analyzing biological targets comprising:

a first member having a cavity formed therewithin;

a workbench member having at least a portion thereof positioned and located within the cavity of said first member so as to divide the cavity of said first member into a first cavity portion and a second cavity portion, at least a portion of said workbench member being movable between a first position wherein said workbench member extends perpendicular to said first and second cavity portions and a second position wherein at least a portion of said workbench member lies adjacent to one of said first and second cavity portions;

a second member hingedly attached to said first member, said second member being movable between a first position wherein said second member overlays the first member and closes access to said first member and a second position wherein said second member provides access to said first member, said second member having at least one cavity formed therewithin, said at least one cavity associated with said second member at least partially receiving said workbench member when said workbench member is in its second position and said second member is in its first position; and at least one leg member for supporting the workbench member in a position perpendicular to said first and second cavity portions of said first member;

wherein said at least one leg member is pivotally connected to said workbench member.

15. The mobile field-deployable laboratory of claim 1 wherein said at least one leg member is attachable to said workbench member.

16. The mobile field-deployable laboratory of claim 1 wherein one of said first and second cavity portions of said first member includes a power supply.

17. The mobile field-deployable laboratory of claim 16 including at least one power outlet associated with said first member, said power supply being electrically connected to said at least one power outlet.

18. The mobile field-deployable laboratory of claim 17 wherein said at least one power outlet includes a plurality of power outlets.

19. A mobile field-deployable laboratory for detecting and analyzing biological targets comprising:

a first member having a cavity formed therewithin;

a workbench member having at least a portion thereof positioned and located within the cavity of said first member so as to divide the cavity of said first member into a first cavity portion and a second cavity portion, at least a portion of said workbench member being movable between a first position wherein said workbench member extends perpendicular to said first and second cavity portions and a second position wherein at least a portion of said workbench member lies adjacent to one of said first and second cavity portions;

a second member hingedly attached to said first member, said second member being movable between a first position wherein said second member overlays the first member and closes access to said first member and a second position wherein said second member provides access to said first member, said second member having at least one cavity formed therewithin, said at least one cavity associated with said second member at least partially receiving said workbench member when said workbench member is in its second position and said second member is in its first position; and at least one leg member for supporting the workbench member in a position perpendicular d cavity portions of said first member;

wherein said workbench member includes a first workbench portion fixedly attached to said first member and a second workbench portion pivotally attached to said first workbench portion.

20. The mobile field-deployable laboratory of claim 19 wherein said workbench member further includes a third workbench portion pivotally attached to said second workbench portion for holding a keyboard.

21. The mobile field-deployable laboratory of claim 20 wherein said third workbench portion includes a first portion hingedly attached to said second workbench portion and a second portion hingedly attached to said first portion.

22. The mobile field-deployable laboratory of claim 1 wherein said at least one cavity of said second member includes at least a portion thereof configured for housing equipment therewithin.

23. The mobile field-deployable laboratory of claim 1 wherein one of said first and second cavity portions of said first member includes a space for housing equipment.

24. A mobile field-deployable laboratory for detection and analysis of biological targets comprising:

a first member having at least one cavity formed therewithin, said at least one cavity including at least one compartment for housing a power supply and least one compartment for housing equipment therewithin;

a workbench member associated with said first member, said workbench member being movable between a first position wherein said workbench member extends perpendicular to said first member and a second position wherein at least a portion of said workbench member lies adjacent to said at least one cavity formed within said first member;

a second member hingedly attached to said first member, said second member being movable between a first position wherein said second member overlays the first member and closes access to said first member and a second position wherein said second member permits access to said first member, said second member having at least one cavity formed therewithin, said at least one cavity formed within said second member at least partially receiving said workbench member and said at least one compartment housing a power supply and said at least one compartment for housing equipment therewithin when said second member is in its first position;

at least one leg member for supporting the workbench member in a position perpendicular to said at least one cavity formed within said first member; and a mobile backpack unit associated with at least a portion of said at least one cavity formed within said first member, said mobile backpack unit being configured for housing ancillary equipment and being at least partially receivable by said at least one cavity of said second member when said second member is in its first position, said mobile backpack unit opening into the at least one cavity of said second member when said second member is in its second position.

25. The mobile field-deployable laboratory of claim 24 wherein said at least one compartment of said first member for housing equipment is configured for housing a cooling system.

26. The mobile field-deployable laboratory of claim 25 wherein said cooling system includes a phase-change cooling system capable of holding a predetermined selected temperature constant for a predetermined time period.

27. The mobile field-deployable laboratory of claim 24 wherein the mobile backpack unit includes a first backpack member and a second backpack member, the first backpack member being receivable within said at least one cavity of said first member and the second backpack member being receivable within the at least one cavity of said second member when said second member is in its second position.

28. The mobile field-deployable laboratory of claim 24 including a computer system for analyzing biological target agents, said computer system including a monitor structure attachable to said first member.

29. The mobile field-deployable laboratory of claim 28 wherein said computer monitor structure includes a computer display screen, a modem, a CPU unit, and a power supply for the CPU unit.

30. The mobile field-deployable laboratory of claim 24 wherein said mobile backpack unit includes a Polymerase Chain Reaction ("PCR") system.

31. The mobile field-deployable laboratory of claim 24 wherein said mobile backpack unit houses a DNA sequencing system.

32. The mobile field-deployable laboratory of claim 24 including a windshield member attachable to at least a portion of said workbench member.

33. The mobile field-deployable laboratory of claim 24 wherein said at least one leg member includes a pair of extendable leg members for supporting the workbench member in a position perpendicular to said first member.

34. The mobile field-deployable laboratory of claim 24 including a power strip associated with said first member, said power strip including a plurality of power outlets.

35. A mobile field-deployable laboratory for detection and analysis of biological targets comprising:

a first member having at least one cavity formed therewithin, said at least one cavity including at least one compartment for housing a power supply and at least one compartment for housing a cooling system;

a workbench member associated with said first member, said workbench member being movable between a first position wherein said workbench member extends perpendicular to said first member and a second position wherein at least a portion of said workbench member lies adjacent to said at least one cavity formed within said first member;

a second member hingedly attached to said first member, said second member being movable between a first position wherein said second member overlays said first member and closes access to said first member and a second position wherein said second member permits access to said first member, said second member having at least one cavity formed therewithin, said at least one cavity formed within said second member at least partially receiving said workbench member and said at least one compartment housing a power supply and said at least one compartment for housing a cooling system when said second member is in its first position;

at least one leg member for supporting the workbench member in a position perpendicular to said first member;

a mobile backpack unit associated with at least a portion of said at least one cavity formed within said first member, said mobile backpack unit being configured for housing ancillary equipment and being at least partially receivable by said at least one cavity of said second member when said second member is in its first position, said mobile backpack unit opening into the at least one cavity of said second member when said second member is in its second position, said mobile backpack unit being removable from said first and second members; and a computer system for analyzing biological target agents, said computer system including a computer monitor structure attachable to said first member, said computer monitor structure including a computer display screen, a modem, a CPU unit, and a power supply for the CPU unit.

* * * * *